(12) United States Patent  (10) Patent No.: US 9,243,269 B2
Zhan  (45) Date of Patent: Jan. 26, 2016

(54) METHODS AND COMPOSITIONS FOR PRODUCTION OF BLUE PIGMENT INDIGOIDINE

(71) Applicant: Jixun Zhan, North Logan, UT (US)

(72) Inventor: Jixun Zhan, North Logan, UT (US)

(73) Assignee: Utah State University, North Logan, UT (US)

( * ) Notice: Subject to any disclaimer, the term of this patent is extended or adjusted under 35 U.S.C. 154(b) by 0 days.

(21) Appl. No.: 14/080,024

(22) Filed: Nov. 14, 2013

(65) Prior Publication Data

US 2014/0142314 A1    May 22, 2014

Related U.S. Application Data

(60) Provisional application No. 61/728,721, filed on Nov. 20, 2012.

(51) Int. Cl.
| | |
|---|---|
| *C12P 17/16* | (2006.01) |
| *C07D 213/90* | (2006.01) |
| *C12N 1/00* | (2006.01) |
| *C12N 15/52* | (2006.01) |

(52) U.S. Cl.
CPC ............ *C12P 17/165* (2013.01); *C07D 213/90* (2013.01); *C12N 1/00* (2013.01); *C12N 15/52* (2013.01)

(58) Field of Classification Search
None
See application file for complete search history.

(56) References Cited

U.S. PATENT DOCUMENTS

2013/0260436 A1* 10/2013 Ackerley et al. ............... 435/193

OTHER PUBLICATIONS

Yu et al., "An indigoidine biosynthetic gene cluster from Streptomyces chromofuscus ATCC 49982 contains an unusual IndB homologue", Journal of Industrial Microbiology and Biotechnology, vol. 40, pp. 159-168, 2013; published online Oct. 10, 2012.*
Komaki et al., "Genome-wide survey of polyketide synthase and nonribosomal peptide synthetase gene clusters in Streptomyces turgidiscabies NBRC 16081", Journal of General and Applied Microbiology, vol. 58, pp. 363-372, 2012.*
Guo et al., "Protein tolerance to random amino acid change", Proceedings of the National Academy of Sciences USA, vol. 101, No. 25, pp. 9205-9210, 2004.*
Aziz, R., et al., The RAST server: Rapid annotations using subsystems technology, BMC Genomics, 2008, vol. 9, article 75.
Bibb, M., Regulation of secondary metabolism in streptomycetes, Current Opinion in Microbiology, 2005, p. 208-215, vol. 8, iss. 2.
Brachmann, A., et al., Triggering the production of the cryptic blue pigment indigoidine from Photorhabdus luminescens, Journal of Biotechnology, Jan. 2012, p. 96-99, vol. 157, iss. 1.

(Continued)

*Primary Examiner* — Robert Mondesi
*Assistant Examiner* — Richard Ekstrom

(57) ABSTRACT

The present disclosure provides for an expression system for the production of blue pigment indigoidine. The system comprises a heterologous host cell, a DNA sequence encoding a Sc-IndB protein, and a DNA sequence encoding a Sc-IndC protein. The system may be configured for the co-expression of the Sc-IndB and Sc-IndC. DNA sequences encoding the Sc-IndB and Sc-IndC may be provided on at least one vector. Alternatively, the DNA sequences encoding the Sc-IndB and Sc-IndC may optionally be integrated into the genome of the heterologous host genome. The expression system may further comprise a sfp gene or a PPTase.

18 Claims, 13 Drawing Sheets

(56) References Cited

OTHER PUBLICATIONS

Chu, M., et al., Unique features of Erwinia chrysanthemi (Dickeya dadantii) RA3B genes involved in the blue indigoidine production, Microbiological Research, 2010, p. 483-495, vol. 165, iss. 6.

Cude, W., et al., Production of the antimicrobial secondary metabolite indigoidine contributes to competitive surface colonization by the marine roseobacter *Phaeobacter* sp. strain Y4l, Applied and Environmental Microbiology, 2012, p. 4771-4780, vol. 78, iss. 14.

Hu, Z., et al., Enhanced heterologous polyketide production in Streptomyces by exploiting plasmid co-integration, Journal of Industrial Microbiology & Biotechnology, 2003, p. 516-522, vol. 30, iss. 8.

Ishikawa, J., et al., FramePlot: a new implementation of the frame analysis for predicting protein-coding regions in bacterial DNA with a high G+C content, FEMS Microbiology Letters, 1999, p. 251-253, vol. 174, iss. 2.

Kieser, T., Practical Streptomyces Genetics, Norwich: The John Innes Foundation, 2000.

Kobayashi, H., New violet 3,3'-bipyridyl pigment purified from deep-sea microorganism Shewanella violacea DSS12, Extremophiles, 2007, p. 245-250, vol. 11, iss. 2.

Koguchi, Y., et al., Trichostatin A and herboxidiene up-regulate the gene expression of low density lipoprotein receptor, Journal of Antibiotics, 1997, p. 970-971, vol. 50, iss. 11.

Khun, R., et al., Indigoidine and other bacterial pigments related to 3,3'-bipyridine, Archive fur Mikrobiolodie, 1965, p. 71-84, vol. 51, iss. 1.

Miller-Wideman, M., et al., Herboxidiene, a new herbicidal substance from Streptomyces chromofuscus A7847 taxonomy, fermentation, isolation, physicochemical and biological properties, Journal of Antibiotics, 1992, p. 914-921, vol. 45, iss. 6.

Muller, M., et al., A novel reporter system for bacterial and mammalian cells based on the non-ribosomal peptide indigoidine, Metabolic Engineering, 2012, p. 325-335, vol. 14, iss. 4.

Novakova, R., et al., Identification and characterization of an indigoidine-like gene for a blue pigment biosynthesis in Streptomyces aureofaciens CCM 3239, Folia Microbiolgica, 2010, p. 119-125, vol. 55, iss. 2.

Oja, T., et al., Characterization of the alnumycin gene cluster reveals unusual gene products for pyran ring formation and dioxan biosynthesis, Chemistry & Biology, 2008, p. 1046-1057, vol. 15, iss. 10.

Owen, J., et al., Rapid and flexible biochemical assays for evaluating 4'-phosphopantetheinyl transferase activity, Biochemical Journal, 2011, p. 709-717, vol. 436, iss. 3.

Pfeifer, B., et al., Biosynthesis of complex polyketides in a metabolically engineered strain of *E. coli*, Science, 2001, p. 1790-1792, vol. 291.

Reverchon S., et al., Characterization of indigoidine biosynthetic genes in Erwinia chrysanthemi and role of this blue pigment in pathogenicity, Journal of Bacteriology, 2002, p. 654-665, vol. 184, iss. 3.

Shao, L., et al., Identification of the herboxidiene biosynthetic gene cluster in Streptomyces chromofuscus ATCC 49982, Applied and Environmental Microbiology, 2012, p. 2034-2038, vol. 78.

Starr, M., et al., Formation of the blue pigment indigoidine by phytopathogenic Erwinia, Applied Microbiology, 1966, p. 870-872, vol. 14, iss. 6.

Takahashi, H., et al., Cloning and characterization of a Streptomyces single module type non-ribosomal peptide synthetase catalyzing a blue pigment synthesis, Journal of Biological Chemistry, p. 9073-9081, vol. 282, iss. 12.

Walsh, C., et al., Post-translational modification of polyketide and nonribosomal peptide synthases, Current Opinion in Chemical Biology, 1997, p. 309-315, vol. 1, iss. 3.

\* cited by examiner

METHODS AND COMPOSITIONS FOR PRODUCTION OF BLUE PIGMENT INDIGOIDINE

RELATED APPLICATIONS

This application claims the benefit of U.S. Provisional Application No. 61/728,721, filed on Nov. 20, 2012.

BACKGROUND

*Streptomyces* is well-known for the production of structurally diverse natural products, including many industrially important bioactive molecules, such as oxytetracycline, chloramphenicol and bleomycin. Most of these bacterial secondary metabolites are produced by complex biosynthetic pathways encoded by physically clustered genes. Among characterized biosynthetic enzymes, polyketide synthases (PKSs) and non-ribosomal peptide synthetases (NRPSs) are most commonly observed. The blue pigment indigoidine [5,5'-diamino-4,4'-dihydroxy-3,3'-diazadiphenoguinone-(2,2')] was previously isolated from phytopathogenic *Erwinia* and other bacteria. It may be synthesized by condensation of two units of L-glutamine by a 4'-phosphopantetheinyl transferase (PPTase)-activated NRPS, such as IndC from *Erwinia chrysanthemi* and *Streptomyces aureofaciens* CCM 3239 and BpsA from *Streptomyces lavendulae*. Because of the presence in its structure of carbon-carbon double bonds conjugated with a carbonyl group, indigoidine is a powerful radical scavenger that enables phytopathogens to tolerate oxidative stress, organic peroxides and superoxides during the plant defense response. Recently, indigoidine has also been found to possess antimicrobial activity.

*Streptomyces chromofuscus* ATCC 49982 was previously isolated from soil collected from a stand of mixed woods from the Stepping Stone Falls Beach Pond State Park, R.I., USA.

Unfortunately, despite its various utilities, conventional methods for production of indigoidine provide for only limited production, which may limit the industrial use of this promising compound. Mere optimization of conventional methods is unlikely to provide meaningful increases in the production of indigoidine.

SUMMARY

In embodiments, the present disclosure provides an expression system for the production of blue pigment indigoidine [5,5'-diamino-4,4'-dihydroxy-3,3'-diazadiphenoguinone-(2,2')], having a heterologous host cell, a DNA sequence encoding a Sc-IndB protein, and a DNA sequence encoding a Sc-IndC protein. Preferably, the expression system is configured for the co-expression of the Sc-IndB and Sc-IndC. The DNA sequences encoding the Sc-IndB and Sc-IndC proteins may be provided on at least one vector. In some examples, both sequences are provided on a single vector. Alternatively, the DNA sequences encoding the Sc-IndB and Sc-IndC may be integrated into the genome of the heterologous host genome.

In embodiments, expression systems related to the present disclosure may further comprise of a DNA sequence encoding a sfp gene or a PPTase. The sfp gene and PPTase may be endogenous to the host cell. Alternatively, the sfp or PPTase may be exogenous to the host cell.

In embodiments, DNA sequences encoding the Sc-IndB and Sc-IndC are operatively linked to at least one promoter. For example, the DNA sequences encoding the Sc-IndB and Sc-IndC may be operatively linked to a single promoter.

In embodiments, DNA sequences encoding a Sc-IndB protein may provide for a polypeptide having the amino acid sequence set forth in SEQ ID NO:2. For example, the DNA sequence may be the sequence set forth in SEQ ID NO:1.

In embodiments, DNA sequences encoding a Sc-IndC protein provides for a polypeptide having the amino acid sequence set forth in SEQ ID NO:4. For example, the DNA sequence may be the sequence set forth in SEQ ID NO:3.

In embodiments, the present disclosure provides methods for synthesizing a blue pigment indigoidine. Generally, the methods consist of co-expressing a Sc-IndB protein and a Sc-IndC protein in a heterologous host. For example, the host may be a bacterium. The heterologous host may have a nucleotide sequence that encodes a sfp gene and may expresses PPTase. For example, the host may have an exogenous sfp and PPTase. Alternatively, the sfp and PPTase may be exogenous.

In embodiments, the present disclosure provides methods for extracting blue pigment indigoidine from a fermentation broth. The methods may include centrifuging a blue pigment indigoidine fermentation broth by low-speed centrifugation to provide pelleted bacterial cells and a supernatant comprising blue pigment indigoidine, and centrifuging the supernatant at a speed sufficiently high to provide pelleted indigoidine pigments. The methods may further include treating the pelleted indigoidine pigment sequentially with water, methanol, ethyl acetate and hexanes to remove impurities to provide a substantially isolated, substantially pure indigoidine pigment.

BRIEF DESCRIPTION OF THE DRAWINGS

FIG. 1A shows the map of pJV1. pJV1 was constructed by cloning Sc-indA into the cloning vector pJET1.2. FIG. 1B shows the map of pJV2. pJV2 was constructed by cloning Sc-indB into the cloning vector pJET1.2. FIG. 1C shows the map of pJV3. pJV3 was constructed by cloning Sc-indC into the cloning vector pJET1.2. FIG. 1D shows the map of pDY49. pDY49 was constructed by ligating Sc-indC into pRM5. FIG. 1E shows the map of pJV6. pJV6 was constructed by ligating Sc-indC into pET28a. FIG. 1F shows the map of pDY52. pDY52 was constructed by ligating Sc-indA into pACYCDuet-1. FIG. 1G shows the map of pDY53. pDY53 was constructed by ligating Sc-indB into pACYC-Duet-1. FIG. 1H shows the map of pDY54. pDY54 was constructed by ligating both Sc-indA and Sc-indB into pACYC-Duet-1.

DETAILED DESCRIPTION

Figure 1A:
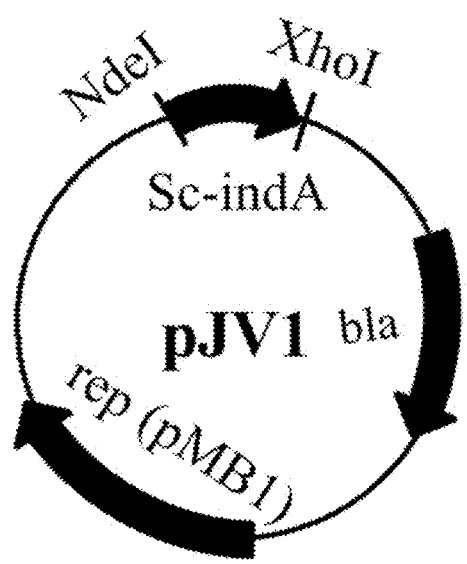
FIGS. 1A through 1H depict exemplary plasmids constructed for cloning and expression of biosynthetic genes.
Figure 1B:
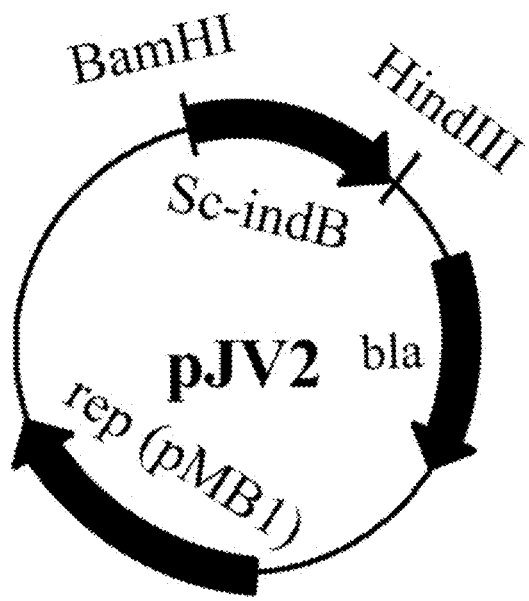
Figure 1C:
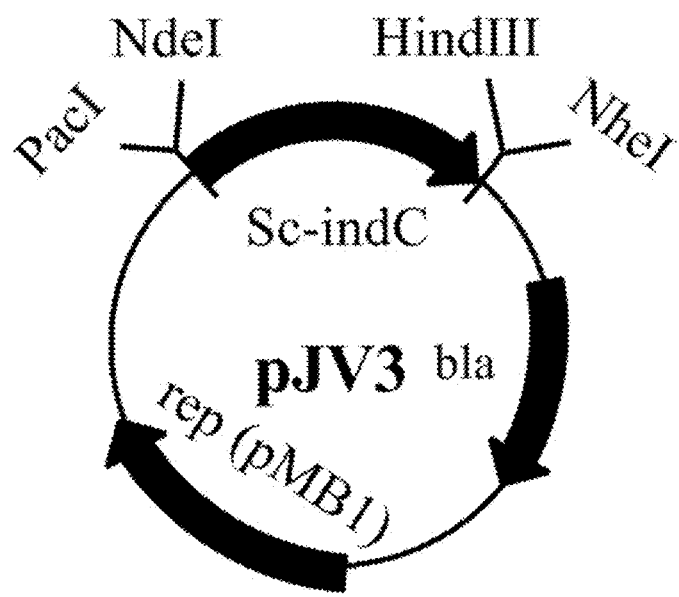
Figure 1D:
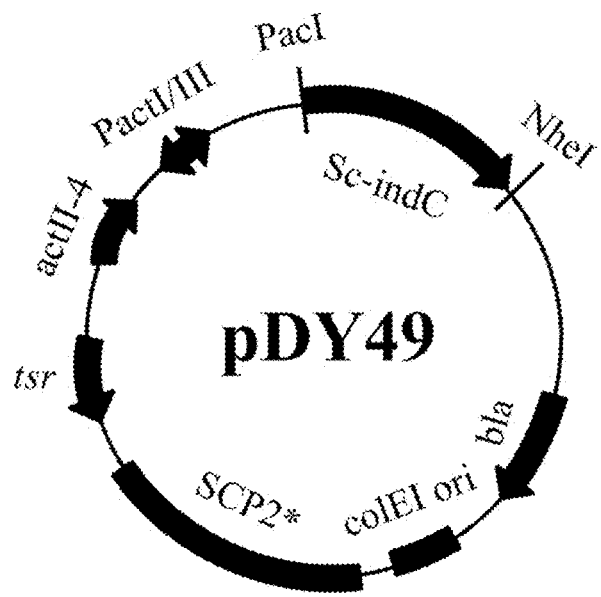
Figure 1E:
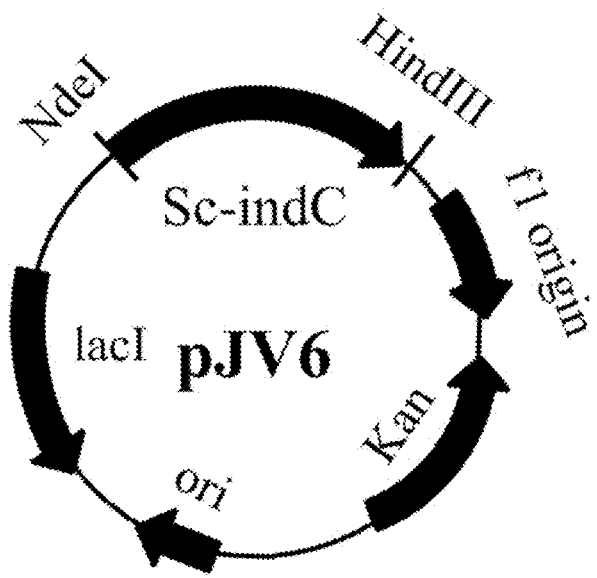
Figure 1F:
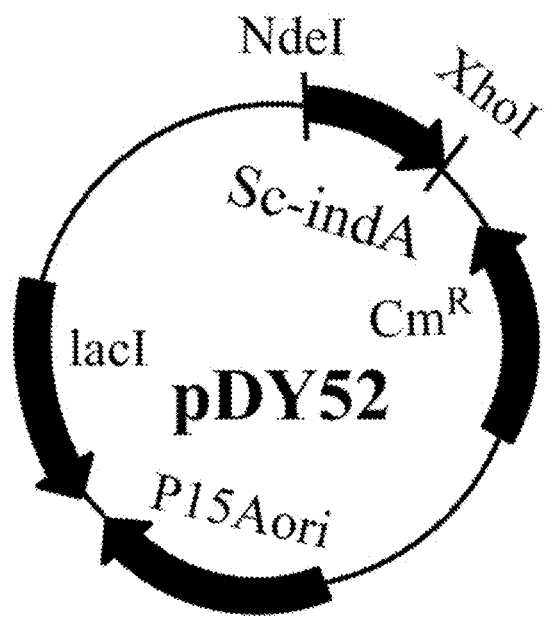
Figure 1G:
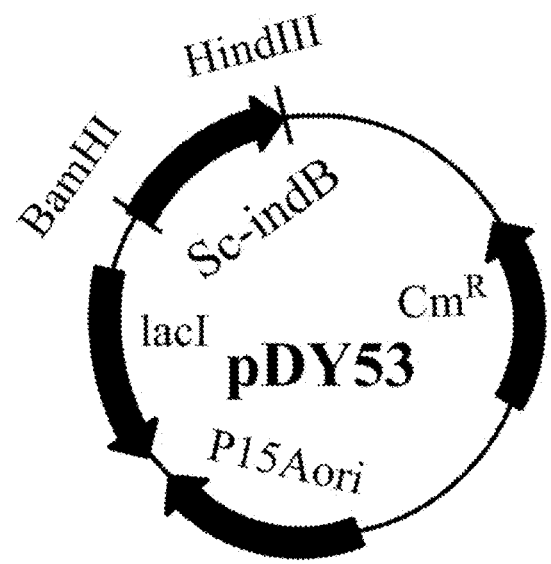
Figure 1H:
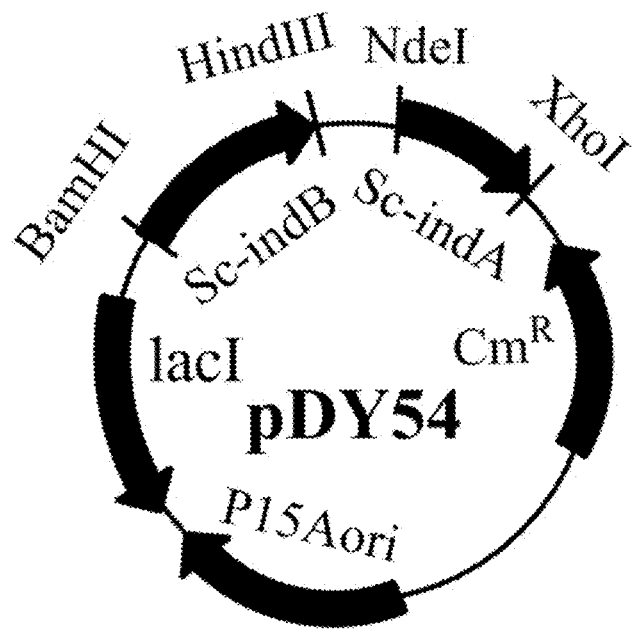

The invention related to the present disclosure overcomes the problems associated with limited production, by providing methods and compositions useful for the increased production and extraction of the natural blue pigment indigoidine [5,5'-diamino-4,4'-dihydroxy-3,3'-diazadiphenoquinone-(2,2')]. In the following description, numerous specific details are provided for a thorough understanding of specific preferred embodiments. However, those skilled in the art will recognize that embodiments can be practiced without one or more of the specific details, or with other methods, components, materials, etc. In some cases, well-known structures, materials, or operations are not shown or described in detail in order to avoid obscuring aspects of the preferred embodiments. Furthermore, the described features, structures, or characteristics may be combined in any suitable manner in a variety of alternative embodiments. Thus, the following more detailed description of the embodiments of the present invention, as illustrated in some aspects in the drawings, is not intended to limit the scope of the invention, but is merely representative of the various embodiments of the invention.

In this specification and the claims that follow, singular forms such as "a," "an," and "the" include plural forms unless the content clearly dictates otherwise. All ranges disclosed herein include, unless specifically indicated, all endpoints and intermediate values. In addition, "optional" or "optionally" refer, for example, to instances in which subsequently described circumstance may or may not occur, and include instances in which the circumstance occurs and instances in which the circumstance does not occur. The terms "one or more" and "at least one" refer, for example, to instances in which one of the subsequently described circumstances occurs, and to instances in which more than one of the subsequently described circumstances occurs.

Expression System Configured to Co-Express Sc-IndB and Sc-IndC

The genes were amplified from the genomic DNA of *S. chromofuscus* ATCC 49982 and ligated into a cloning vector such as pJET1.2 for sequencing. The Sc-indC was ligated into expression vectors such as pRM5 and pET28a to yield pDY49 and pJV6. Sc-indA and Sc-indB are ligated into an expression vector such as pACYCDuet-1 to yield pDY52, pDY53 and pDY54 (for plasmids constructed for cloning and expression of biosynthetic genes, see FIGS. 1A-1H).

In embodiments, the present disclosure provides for an expression system useful for the production of the blue pigment indigoidine. Components of the expression system may include a host cell, a Sc-IndC protein, a nucleotide sequence encoding the Sc-IndC, a Sc-IndB protein, and a nucleotide sequence encoding the Sc-IndB. The nucleotide sequences may be provided on a single vector or multiple vectors. The nucleotide sequences may be operatively linked to a promoter or promoters. For example, nucleotide sequences encoding Sc-IndC and Sc-IndB, and the promoter sequence, may be configured for the transcription of each gene to be driven by a single promoter. Alternatively, the genes may be configured such that different promoters drive the transcription of each gene.

In embodiments, the genes encoding Sc-IndC and Sc-IndB are provided on at least one vector. Preferably, the genes are provided on a single vector. Alternatively, the nucleotide sequences encoding the Sc-IndC and Sc-Ind B proteins may be incorporated in a host genome. Vectors may include pET28, pACYCDuet-1, pRM5 and other expression or integration vectors.

In embodiments, expression systems of the present disclosure include a heterologous host cell. Host cells may include bacteria, yeast, or mammalian cells. Preferably, host cells may have an endogenous PPTase that contributes to the activation of the T domain of Sc-IndC. Alternatively, an exogenous PPTase may be provided as part of the expression system. For example, PPTase may be provided on the same vector that provides for at least one of Sc-IndC or Sc-IndB, on a separate vector, or integrated into the host genome.

Polynucleotide and Polypeptide Sequences

It is an object of the present disclosure to provide nucleotide sequences that encode for polypeptides that function in the biosynthesis of blue pigment indigoidine. SEQ ID NO:1 is a DNA sequence that encodes for the polypeptide amino acid sequence SEQ ID NO:2. SEQ ID NO:2 is an amino acid sequence that serves as the primary structure of an exemplary Sc-IndB protein. SEQ ID NO:3 is a DNA sequence that encodes for the polypeptide amino acid sequence SEQ ID NO:4. SEQ ID NO:4 is an amino acid sequence that serves as the primary structure of an exemplary Sc-IndC protein.

It is a further object of this disclosure to provide functional equivalents of the listed isolated nucleic acid molecules and derivatives thereof. For example, the nucleic acid sequences depicted in SEQ ID NO:1 or SEQ ID NO:3 can be altered by substitutions, additions or deletions that provide for functionally equivalent molecules. Due to the degeneracy of nucleotide coding sequences, other DNA sequences which encode substantially the same amino acid sequence as depicted in SEQ ID NO:1 and SEQ ID NO:3 can be used in the practice of the present invention. These include but are not limited to nucleotide sequences comprising all or portions of the nucleic acid depicted in SEQ ID NO:1 and 3, which are altered by the substitution of different codons that encode the same amino acid residue, or a functionally equivalent amino acid residue within the sequence.

It is yet another object of the present disclosure to provide nucleotide sequence which result from the addition, deletion or substitution of at least one nucleotide to the 5'-end and/or the 3'-end of the nucleic acid formula shown in SEQ ID NO:1 and 3, or a derivative thereof. Any nucleotide or polynucleotide can be used in this regard, provided that its addition, deletion or substitution does not substantially alter the amino acid sequence of SEQ ID NO:2, or SEQ ID NO:4 which is encoded by the nucleotide sequence. Moreover, the nucleic acid molecule of the present invention can, as necessary, have restriction endonuclease recognition sites added to its 5'-end and/or 3'-end. Examples of 5'-end and 3'-end modifications include the introduction of additional nucleotides including ribosomal binding sites and various protein tags.

Further, it is possible to delete codons or to substitute one or more codons by codons other than degenerate codons to produce a structurally modified polypeptide, but one which has substantially the same utility or activity of the polypeptide produced by the unmodified nucleic acid molecule. As recognized in the art, the two polypeptides are functionally equivalent, as are the two nucleic acid molecules which give rise to their production, even though the differences between the nucleic acid molecules are not related to degeneracy of the genetic code.

As used herein, terms herein referring to nucleic acid molecules such as "isolated polynucleotide molecule," "DNA sequence," and "nucleotide sequence", and the like, unless otherwise specified, include both single-stranded and double-stranded DNA molecules. Any reference to a "Sequence Listing" or a "SEQ ID NO" is intended to refer to both the DNA of the "Sequence Listing" includes sequences complementary to the DNA sequences.

References to sequences homologous to a sequence, or sequence listing, are to be understood to include sequences homologous to a sequence corresponding to the referenced sequence and sequences homologous to a sequence complementary to the referenced sequence.

Polynucleotide molecules of the present invention include both synthetic molecules and molecules obtained through recombinant techniques, such as by in vitro cloning and transcription.

For purposes of the present disclosure, the nucleotide sequence of a second polynucleotide molecule is "homologous" to the nucleotide sequence of a first polynucleotide molecule where the nucleotide sequence of the second polynucleotide molecule encodes the same polypeptide as the nucleotide sequence of the first polynucleotide molecule as based on the degeneracy of the genetic code, or when it encodes a polypeptide that is sufficiently similar to the polypeptide encoded by the nucleotide sequence of the first polynucleotide molecule so as to provide at least one in-vivo or in-vitro biological function that corresponds to a function of the polypeptide encoded by the nucleotide sequence of the first polynucleotide molecule and identified in the present disclosure. Generally, the nucleotide sequence of a second polynucleotide molecule is homologous to the nucleotide sequence of a first polynucleotide molecule if it has at least about 70% nucleotide sequence identity to the nucleotide sequence of the first polynucleotide molecule as based on the BLASTN algorithm (National Center for Biotechnology Information, otherwise known as NCBI, (Bethesda, Md., USA) of the United States National Institute of Health). Preferably, a homologous nucleotide sequence has at least about 75% nucleotide sequence identity, even more preferably at least about 85% nucleotide sequence identity. Since the genetic code is degenerate, a homologous nucleotide sequence can include any number of "silent" base changes, i.e. nucleotide substitutions that nonetheless encode the same amino acid. A homologous nucleotide sequence can further contain non-silent mutations, i.e. base substitutions, deletions, or additions resulting in amino acid differences in the encoded polypeptide, so long as the polypeptide sequence remains at least about 70% identical to the polypeptide encoded by the first nucleotide sequence or otherwise provides at least one in-vivo or in-vitro biological function that corresponds to a function of the polypeptide encoded by the nucleotide sequence of the first polynucleotide molecule.

Homologous nucleotide sequences can be determined by comparison of nucleotide sequences, for example by using BLASTN, above. Alternatively, homologous nucleotide sequences can be determined by hybridization under selected conditions. For example, the nucleotide sequence of a second polynucleotide molecule is homologous to SEQ ID NO:1 if it hybridizes to the complement of SEQ ID NO:1 under moderately stringent conditions, e.g., hybridization to filter-bound DNA in 0.5 M NaHPO.sub.4, 7% sodium dodecyl sulfate (SDS), 1 mM EDTA at 65.degree. C., and washing in 0.2.times.SSC/0.1.degree./0 SDS at 42.degree. C., or conditions that will otherwise result in hybridization of sequences. In another embodiment, a second nucleotide sequence is homologous to SEQ ID NO:1 if it hybridizes to the complement of SEQ ID NO:1 under highly stringent conditions, e.g. hybridization to filter-bound DNA in 0.5 M NaHPO.sub.4, 7% SDS, 1 mM EDTA at 65.degree. C., and washing in 0.1.times.SSC/0.1% SDS at 68.degree. C.

Production of Indigoidine by Co-Expression of Sc-IndC and Sc-IndB

In one embodiment, the present disclosure provides methods of co-expressing Sc-IndC and Sc-IndB proteins to upregulate the production of a blue pigment indigoidine in a heterologous host. The methods are based, in part, on the unexpected discovery that co-expressing Sc-IndC and Sc-IndB proteins can greatly increase the yield of the blue pigment indigoidine. For example, the production of blue pigment indigoidine may be carried out by co-expressing Sc-IndC and Sc-IndB proteins in *E. coli*. Generally, the methods described herein provide for increased yield when compared to conventional methods. Preferably, the increased yield is higher than the yield observed for Sc-IndC or Sc-IndB expressed alone.

Exemplary fermentation conditions for the synthesis of the blue pigment indigoidine are provided herein. The exemplary fermentation conditions are provided in order to give guidance to those in the art who want to explore the broad concepts presented herein, and are not intended to limit the scope of the embodiments of the invention that are related to co-expressing Sc-IndC and Sc-IndB proteins.

Sequencing and Nucleotide Sequence Discovery

The present disclosure describes the discovery of a 9.4-kb biosynthetic gene cluster from *S. chromofuscus* ATCC 49982 that contains five open reading frames (ORFs), including a putative indigoidine synthase gene, designated Sc-indC. The Sc-indC gene and two other genes from the same gene cluster, Sc-indA and Sc-indB, were cloned. The identification of Sc-indB ultimately contributed to the discovery that co-expressing Sc-IndB and Sc-IndC, in a heterologous host, provides for the upregulation of the expression of the blue pigment indigoidine.

The present disclosure also provides for isolated, cDNA nucleotide sequences, related to SEQ ID NO: 1, which encode Sc-IndB proteins having an amino acid sequence related to SEQ ID NO: 2. SEQ ID NO: 1 is an exemplary sequence for providing an Sc-IndB protein, and is not necessarily intended to limit the scope to the present invention. Due to the degeneracy of the genetic code, various modifications to SEQ ID NO: 1 would result in the same polypeptide sequence of amino acids, and thus the same Sc-IndB protein, as provided by SEQ ID NO: 1. For the purpose of the present invention, it is sufficient that a nucleotide sequence encode for a Sc-IndB protein, or a functional sub-unit of a Sc-IndB protein. Preferably, the Sc-IndB protein comprises the polypeptide amino acid sequence shown in SEQ ID NO: 2.

Expression of Sc-IndC

Heterologous expression of Sc-IndC in *S. coelicolor* CH999 and *E. coli* BAP1 demonstrated that Sc-IndC is responsible, at least in part, for the synthesis of the blue pigment indigoidine. The fermentation conditions for indigoidine production in *E. coli* BAP1 were studied and optimized. The engineered *E. coli* BAP1 strain that expresses Sc-IndC may be grown in a fermentation medium such as LB medium. When the $OD_{600}$ reaches 0.4~1.0, an inducer such as isopropyl-1-thio-β-D-galactopyranoside (IPTG) and lactose will be added to induce protein expression and indigoidine production. The induced fermentation broth may be maintained at a temperature between 16 and 28° C. for 10~20 hrs. Generally, any temperature suitable for fermentation may be used. Applicant has unexpectedly discovered, and the present disclosure provides, methods for production of blue pigment indigoidine comprising co-expressing Sc-IndC and Sc-IndB proteins that result in higher yields than those achieved with conventional methods.

Bacterial Strains, Vectors, and Culture Conditions

Any suitable bacterial strain, vector or culture condition may be used for the synthesis of the blue pigment indigoidine. By way of example, suitable bacterial strains include *E. coli* strains. Alternatively, any species or strain of *Streptomyces* may be used. Broadly, a suitable bacterial strain is any strain capable of expressing Sc-IndB and Sc-IndC proteins. There is no requirement that the mere expression of Sc-IndB and Sc-IndC proteins in a suitable bacterial strain result in the synthesis of the blue pigment indigoidine. It is acceptable that the suitable bacterial strain may require further engineering for the expression of Sc-IndB and Sc-IndC proteins to result in the synthesis of the blue pigment indigoidine. Preferably, the suitable bacterial strain may be pre-engineered to synthesize the blue pigment indigoidine when expression of Sc-IndB and Sc-IndC proteins are co-expressed. In some embodiments, Sc-IndB proteins and Sc-IndC proteins may be provided by a vector or vectors that encode for the proteins. The vector or vectors may be plasmids.

Extraction Methods

The present disclosure also provides a new, efficient and economical extraction and purification method for indigoidine. The first step is to remove *E. coli* cells from the fermentation broth by low-speed centrifugation. At a low centrifugation speed, the cells will be pelleted while indigoidine stays in the supernatant. The supernatant will be transferred into a new centrifugation tube and will be further centrifuged at a much higher speed to pellet indigoidine. This settled blue pigment will then successively be washed with water, methanol, ethyl acetate and hexanes to remove impurities to afford pure indigoidine.

The present disclosure also provides for the sequencing of a genome of *S. chromofuscus* ATCC 49982. Sequencing of the genome of *S. chromofuscus* ATCC 49982 led to the identification a noniterative type I polyketide biosynthetic gene cluster that is responsible for the biosynthesis of herboxidiene.

The present disclosure also provides for the discovery of a 9.4-kb biosynthetic gene cluster from *S. chromofuscus* ATCC 49982 that contains five open reading frames (ORFs), including a putative indigoidine synthase gene, designated Sc-indC. The Sc-indC gene and two other genes from the same gene cluster, Sc-indA and Sc-indB, were cloned.

The following examples are illustrative only and are not intended to limit the disclosure in any way. One skilled in the art would recognize various known methods and conditions for expressing or co-expressing proteins, for carrying out fermentation, and for extractions. Each of these various embodiments are within the scope of the invention.

EXAMPLES

The following material and methods may be used in carrying out the various embodiments of the invention.

Example 1

Bacterial Strains, Vectors, and Culture Conditions

*S. chromofuscus* ATCC 49982 was obtained from the American Type Culture Collection (ATCC). It was grown at 30° C. in YEME medium for the preparation of genomic DNA. *S. coelicolor* CH999 and *E. coli* BAP1 were obtained from Stanford University. *S. coelicolor* CH999 was grown in R5 medium at 30° C. The pRM5-derived plasmid pJX28 carrying the thiostrepton-resistance gene was used as an *E. coli/Streptomyces* shuttle vector to express Sc-IndC in *S. coelicolor* CH999. For the blue pigment synthesis, the engineered strain of *S. coelicolor* CH999 was cultured at 30° C. in R5 medium supplemented with 50 μg/ml thiostrepton.

*E. coli* XL1-Blue (Agilent) and pJET1.2 (Fermentas) were used for DNA cloning and sequencing. *E. coli* BAP1 and pET28a (Novagen) were used for protein expression and pACYCDuet-1 (Novagen) was used for the co-expression experiments. *E. coli* cells were grown in Luria-Bertani (LB) medium. When necessary, appropriate antibiotics were added at the following concentrations: ampicillin, 50 μg/ml; kanamycin, 50 μg/ml; and chloramphenicol, 25 μg/ml. For protein expression and product synthesis, 200 μM of IPTG was added into the *E. coli* BAP1 cultures for induction.

Example 2

DNA Manipulations

The genomic DNA of *S. chromofuscus* was isolated using standard methods. Plasmids in *E. coli* were extracted using a GeneJET™ Plasmid Miniprep Kit (Fermentas).

Example 3

Genome Sequencing and Homology Analysis of the Predicted Proteins

The genomic DNA of *S. chromofuscus* ATCC 49982 was sequenced using a 454 GS FLX+ next-generation DNA sequencer and annotated with RAST (Rapid Annotation using Subsystem Technology). The 9,457-kb indigoidine biosynthetic gene cluster was further analyzed through Frame-Plot and BLAST, and was deposited in GenBank under accession number JX499187.

Example 4

Expression of Sc-IndC in *S. coelicolor* CH999

The gene Sc-indC was amplified by PCR from the genome of *S. chromofuscus* ATCC 49982 with Phusion® Hot Start High-Fidelity DNA Polymerase (New England Biolabs) using a pair of primers, 5'-aa<u>TTAATTAAGGAGGAGCCCAT</u>atgagcgtagagaccatccc-3' (the PacI and NdeI sites are underlined) and a 5'-aa<u>GCTAGCAAGCTT</u> tcagtagt-tgggcgtcttgc-3' (the NheI and HindIII sites are underlined).

The amplified Sc-indC was ligated into the cloning vector pJET1.2 to yield pJV3 (Table 1).

TABLE 1

Description of plasmids constructed.

| Plasmid | Description |
|---------|-------------|
| pJV1 | Sc-indA in pJET1.2 |
| pJV2 | Sc-indB in pJET1.2 |
| pJV3 | Sc-indC in pJET1.2 |
| pDY49 | Sc-indC in pRM5 |
| pJV6 | Sc-indC in pET28a |
| pDY52 | Sc-indA pACYCDuet-1 |
| pDY53 | Sc-indB in pACYCDuet-1 |
| pDY54 | Sc-indA and Sc-indB in pACYCDuet-1 under two separated T7 promoters |

The Sc-indC insert was excised from pJV3 with PacI and NheI and ligated into pJX28 between the same sites to generate pDY49 (Table 1). The plasmid was introduced into *S. coelicolor* CH999 by protoplast transformation, and confirmed transformants were selected on R5 agar containing 50 µg/ml thiostrepton after 5~7 days of incubation at 30° C. The correct transformant was grown in 50 ml of R5 medium supplemented with 50 µg/ml thiostrepton, which was maintained at 30° C. with shaking at 250 rpm for 5~7 days to produce indigoidine.

Example 5

Expression of Sc-IndC in *E. coli* BAP1

The Sc-indC gene was excised from pJV3 by digestion with NdeI and HindIII and inserted into the same sites of pET28a to generate pJV6 (Table 1). The plasmid was introduced into *E. coli* BAP1 and correct transformants were selected on LB agar supplemented with 50 µg/ml kanamycin. To reconstitute the biosynthesis of indigoidine, the correct transformant was grown in LB broth supplemented with 50 µg/ml kanamycin at 37° C. and 250 rpm. When the OD600 reached 0.4~1.0, 200 µM of IPTG was added to induce the expression of Sc-IndC at a lower temperature (18° C. or 25° C.).

Example 6

Co-Expression of Sc-IndC with Sc-IndA and/or Sc-IndB in *E. coli* BAP1

The Sc-indA gene was amplified by PCR from the *S. chromofuscus* genome using 5'-aaCATatggacgatcccgccccccg-3' (the NdeI site is underlined) and 5'-aatcactggtcttcctcgtc-3'. The amplified Sc-indA gene was ligated with the pJET1.2 vector to yield pJV1 (Table 1). The Sc-indA gene was excised from pJV1 by digestion with NdeI and XhoI (on pJET1.2) and inserted into MCS2 of the pACYCDuet-1 vector between the same sites to yield pDY52 (Table 1). The Sc-indB gene was amplified by PCR from the *S. chromofuscus* genome using 5'-aaGGATCCatgttcgacctggacggaac-3' (the BamHI site is underlined) and 5'-aaAAGCTTtcagtcgaccggggctgct-3' (the HindIII site is underlined). The amplified Sc-indB gene was ligated with the pJET1.2 vector to yield pJV2 (Table 1). After gene sequencing, Sc-indB was excised from pJV2 by digestion with BamHI and HindIII and inserted into MCS1 of the pACYCDuet-1 vector between the same sites to yield pDY53 (Table 1). The Sc-indA gene was excised from pJV1 using NdeI and BglII (on pJET1.2) and ligated into MCS2 of pDY53 between the same sites to afford pDY54 (Table 1). Each of these pACYCDuet-1 derived plasmids (pDY52, pDY53 and pDY54) was introduced with pJV6 into *E. coli* BAP1. Co-expression experiments of Sc-indC with Sc-indA and/or Sc-indB in *E. coli* BAP1 were performed at 18° C.

Example 7

Extraction and Analysis of Indigoidine

To extract the blue pigment indigoidine, 1 ml of dark blue fermentation broth was taken into a 1.5-ml Eppendorf tube, which was centrifuged at 21,000×g for 10 minutes. The supernatant was discarded, and the pellet was washed with 1 ml of methanol three times with gentle vortexing to remove other metabolites from the cells. By centrifugation at 21,000×g for 10 minutes, the crude blue pigment was collected, dried in vacuo and dissolved in 1 ml of dimethyl sulfoxide by sonication. The dimethyl sulfoxide-insoluble components and cell debris were removed by centrifugation (850×g, 5 minutes). The solution of indigoidine in dimethyl sulfoxide was analyzed on an Agilent 1200 HPLC and 6130 Single Quad LC/MS (C18, 5 µm, 4.6×150 mm column), eluted with a linear gradient of 10-90% aqueous methanol over 25 minutes at a flow rate of 1 ml/min.

Example 8

Preparation of a Standard Curve for Indigoidine to Measure the Yields

To obtain pure indigoidine for a standard curve, the fermentation broth was centrifuged at 850×g for 5 minutes. At this speed, the cells were pelleted while indigoidine still remained in the supernatant. After removal of the cells, the supernatant was further centrifuged at a much higher speed (21,000×g) for 10 minutes to allow indigoidine to settle. This blue pigment was then successively washed twice with water, methanol, ethyl acetate and hexanes to remove impurities, which yielded pure indigoidine.

1 mg of purified indigoidine was dissolved in 1 ml of dimethyl sulfoxide. This solution was then serially diluted into six different concentrations (0.01, 0.025, 0.05, 0.10, 0.20 and 0.25 mg/ml). Each solution was measured for OD600 values on a Thermo Scientific GENESYS 20 Visible Spectrophotometer. The standard curve was established by the linear relationship between the absorbance and concentration.

Example 9

SDS-PAGE Analysis of Protein Expression

The engineered *E. coli* BAP1 strains were grown in 100 ml of LB medium supplemented with appropriate antibiotics and induced with 200 µM IPTG at 18° C. for 12 hours. The cells were collected by centrifugation at 2,700×g for 5 minutes and resuspended in 3 ml of lysis buffer (20 mM Tris-Cl, 500 mM NaCl, pH 7.9). After 10 minutes of ultrasonication (18 W, 30 s of interval), the resultant lysates were centrifuged at 21,000×g for 10 minutes. Insoluble proteins were dissolved in 8 M urea. Both soluble and insoluble fractions were analyzed by 12% SDS-PAGE.

Example 10

Analysis of a Putative Indigoidine Biosynthetic Gene Cluster

Figure 2:
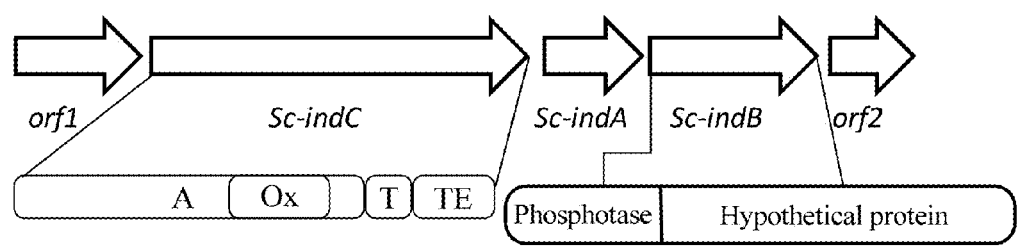
FIG. 2 depicts an exemplary indigoidine biosynthetic gene cluster in *S. chromofuscus* ATCC 49982. The structural organization of Sc-IndC and Sc-IndB is shown. A: adenylation; Ox: oxidation; T: thiolation; TE: thioesterase.

Referring now to FIG. 2, A 9.4-kb putative indigoidine biosynthetic gene cluster was found in the genome of *S. chromofucus* ATCC 49982 (Table 2). It contains five ORFs. The first ORF was named orf1, which encodes a putative transmembrane transporter. The second ORF Sc-indC encodes an indigoidine synthase that is homologous to IndC from *E. chrysanthemi*. IndC is a NRPS that synthesizes indigoidine in *E. chrysanthemi*. Further analysis of Sc-IndC showed that this protein contains an adenylation (A) domain, a thiolation (T) domain, a thioesterase (TE) domain, and an oxidation (Ox) domain that is embedded in the A domain. This structural organization is the same as other homologues such as BpsA from *S. lavendulae* ATCC 11924. Two conserved core motifs, DDFFELGGNSL (963-973) and GYSFG (1099-1103), were found in the T and TE domains, respectively. The A domain has the signature sequence DAWQF-GLINK for recognition of L-glutamine, which is the precursor for indigoidine biosynthesis. This further suggested that Sc-IndC is an indigoidine synthase. The predicted protein product of the third ORF Sc-indA is similar to IndA that was previously found in the indigoidine biosynthetic pathway in *E. chrysanthemi*, although the function of IndA in indigoidine biosynthesis is still unclear. The fourth ORF Sc-indB in this gene cluster encodes a 614-aa protein. Interestingly, the N-terminal portion (1-221 aa) of this unusual protein is a homologue of IdgB from *E. chrysanthemi*, while the C-terminal part (217-614) resembles SclaA2__37635 of *Streptomyces clavuligerus*, which is a hypothetical protein without a known function. IndB and IdgB have been previously reported in the indigoidine biosynthetic pathway in different strains of *E. chrysanthemi*.

Example 11

Reconstitution of Sc-IndC and Indigoidine Biosynthesis in *S. coelicolor* CH999

Unexpectedly, although a putative indigoidine biosynthetic gene cluster was located in the genome of *S. chromofucus* ATCC 49982, no blue pigments were detected from the extract of this bacterium, which indicated that this gene cluster is silent in *S. chromofucus* ATCC 49982 under laboratory conditions. In order to identify the function of Sc-indC, this gene was ligated into an *E. coli*/*Streptomyces* shuttle vector to yield pDY49 (Table 1). This plasmid was introduced through protoplast transformation into *S. coelicolor* CH999.

Figure 3A:
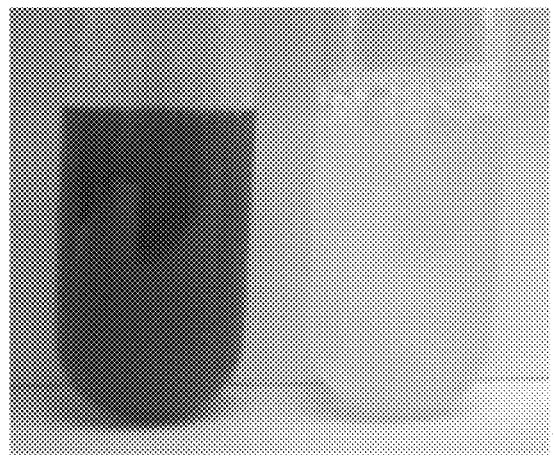
FIG. 3 depicts an exemplary reconstitution of indigoidine biosynthesis in *S. coelicolor* CH999. (A) Production of the blue pigment by *S. coelicolor* CH999/pDY49. The engineered strain was grown in a R5 medium supplemented with 50 μg/ml thiostrepton at 30° C. for 6 days. *S. coelicolor* CH999 harboring the blank shuttle vector was used as the vector control. All experiments were performed in triplicate, and a representative result was shown. (B) Indigoidine extracted from *S. coelicolor* CH999/pDY49 and dissolved in dimethyl sulfoxide. (C) HPLC analysis of the fermentation broth of *S. coelicolor* CH999/pDY49 at 600 nm. (D) UV spectrum of indigoidine.
Figure 3B:
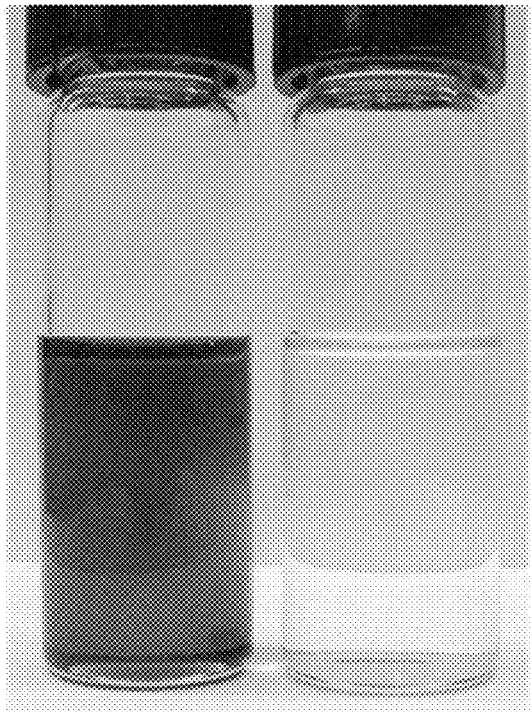
Figure 3C:
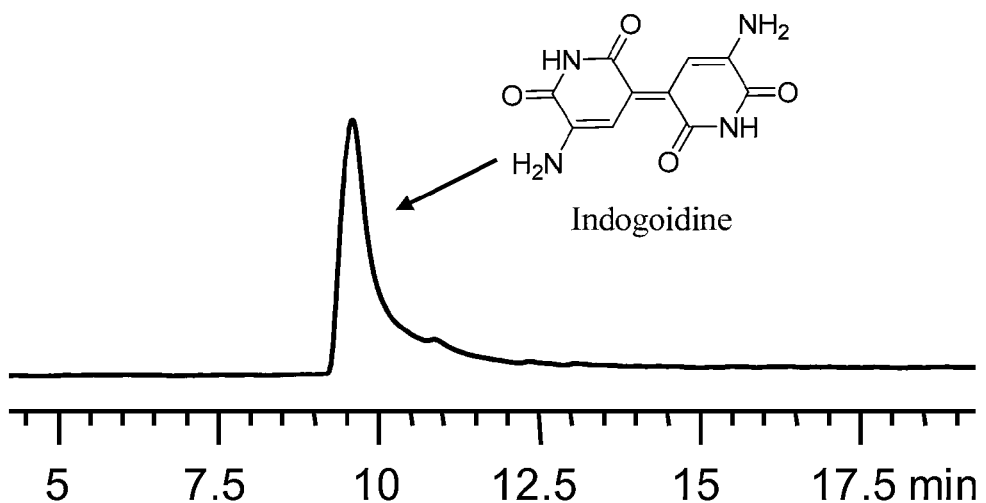
Figure 3D:
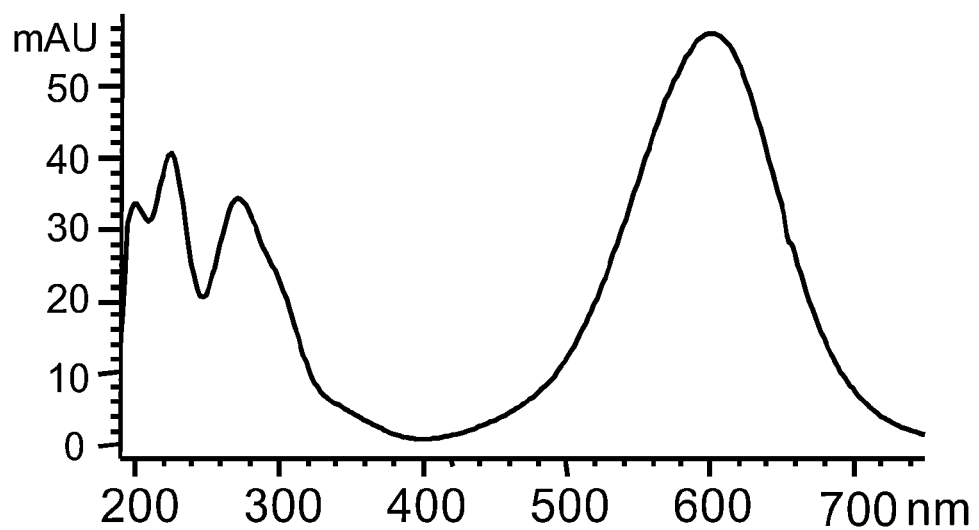

Referring now to FIG. 3, the engineered strain of *S. coelicolor* CH999/pDY49 was grown in R5 medium supplemented with 50 μg/ml thiostrepton at 30° C. and was found to produce a blue pigment (FIG. 3A). The pigment was extracted and re-dissolved in dimethyl sulfoxide, which showed a bright blue color (FIG. 3B). LC-MS analysis of the extracted pigment at 600 nm showed a major peak at 9.64 min (FIG. 3C) that has a maximum UV absorption at 602 nm (FIG. 3D), which is consisted with that of indigoidine. ESI-MS spectrum of this compound showed a $[M+H]^+$ peak at m/z 249, further confirming that this product is indigoidine. Thus, heterologous expression of Sc-indC confers the ability to synthesize indigoidine on *S. coelicolor* CH999. Accordingly, the function of Sc-IndC was characterized as an indigoidine synthase. A standard curve using purified indigoidine was established based on the absorbance at 600 nm and used to quantify the production of this pigment. In *S. coelicolor* CH999, the maximum yield of indigoidine achieved 593.5 mg/l after 6 days of cultivation.

Example 12

Reconstitution of Sc-IndC and Indigoidine Biosynthesis in *E. coli* BAP1

Compared with *Streptomyces*, *E. coli* possesses some advantages such as fast growth rate and high expression level for many heterologous proteins. *E. coli* is commonly used for

TABLE 2

Deduced functions of ORFs in the indigoidine biosynthetic gene cluster

| Gene | No. of amino acids | Protein homologue (accession no.) | % identity/ similarity | Proposed function |
|---|---|---|---|---|
| orf1 | 421 | Transmembrane transporter of *Streptomyces hygroscopicus* ATCC 53653 (EFL27184) | 55/68 | Transmembrane transporter |
| Sc-indC | 1,377 | IndC of *Erwinia chrysanthemi* (CAB87990) | 54/71 | Indigoidine synthase |
| Sc-indA | 317 | IndA of *E. chrysanthemi* (CAB87988) | 65/80 | Hypothetical protein |
| Sc-indB | 614 | 1-221 IdgB of *E. chrysanthemi* (AAF74780) | 51/62 | Predicted phosphatase |
|  |  | 227-614 SclaA2__37635 of *Streptomyces clavuligerus* ATCC 27064 (ZP__08221604) | 54/67 | Hypothetical protein |
| orf2 | 238 | SanR of *Streptomyces ansochromogenes* (AAG48136) | 76/84 | Phosphoribosyl transferase-type I domain |

Figure 4A:
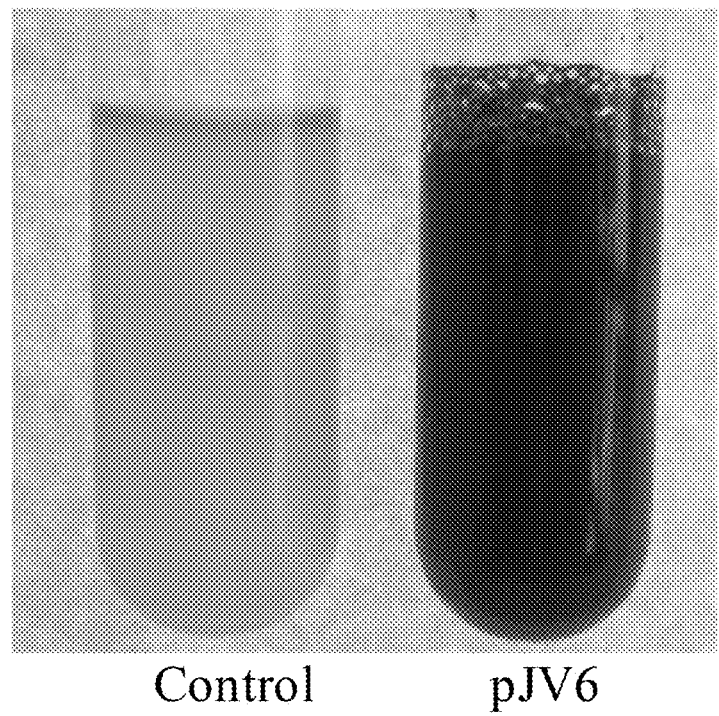
FIG. 4 depicts an exemplary reconstitution of indigoidine biosynthesis in *E. coli* BAP1. (A) Production of indigoidine by *E. coli* BAP1/pJV6. The strain was grown in LB medium supplemented with 50 μg/ml kanamycin at 37° C. and induced with 200 μM IPTG at 25° C. for 13 hours. *E. coli* BAP1/pET28a was used as the vector control. (B) Effect of the OD600 values before induction on the yield of indigoidine. (C) Time-course analysis of indigoidine production at 18° C. and 25° C. (D) Effect of temperatures on the stability of indigoidine. The pigment was stored at room temperature (left) and 4° C. (right) in cell-free LB medium for 2 days. Experiments were performed in triplicate and presented as means±SD (n=3).

In this studied gene cluster, Sc-IndB appears to be a fusion protein of two proteins and it is unknown what role it plays in indigoidine biosynthesis in *S. chromofucus* ATCC 49982. The last ORF is named orf2, which encodes a phosphoribosyl transferase and is homologous to SanR of *Streptomyces ansochromogenes* (Table 2).

heterologous expression of numerous enzymes including NRPSs and synthesis of their products. Because Sc-IndC is a NRPS, its T domain needs to be activated from the apo to holo form to be functional. Accordingly, a dedicated PPTase may be useful to transfer the phosphopantetheinyl group from coenzyme A to a conserved serine residue in the T-domain of Sc-IndC. *E. coli* BAP1 is an engineered strain of *E. coli* BL21(DE3) and harbors a sfp gene encoding a PPTase from *Bacillus subtilis* in the genome. The present disclosure provides for the use of *E. coli* BAP1 as a host to functionally reconstitute Sc-IndC. The Sc-indC gene was ligated into pET28a to yield pJV6 (Table 1), which was introduced into *E. coli* BAP1 for protein expression. As expected, the *E. coli* BAP1 cells transformed with pJV6 produced indigoidine (FIG. 4A). Compared to *S. coelicolor* CH999, the synthesis of this blue pigment in *E. coli* BAP1 is much faster. The blue color could be easily observed in the *E. coli* culture 30 minutes after IPTG induction.

Example 13

Production of Indigoidine in *E. Coli* BAP1

Figure 4B:
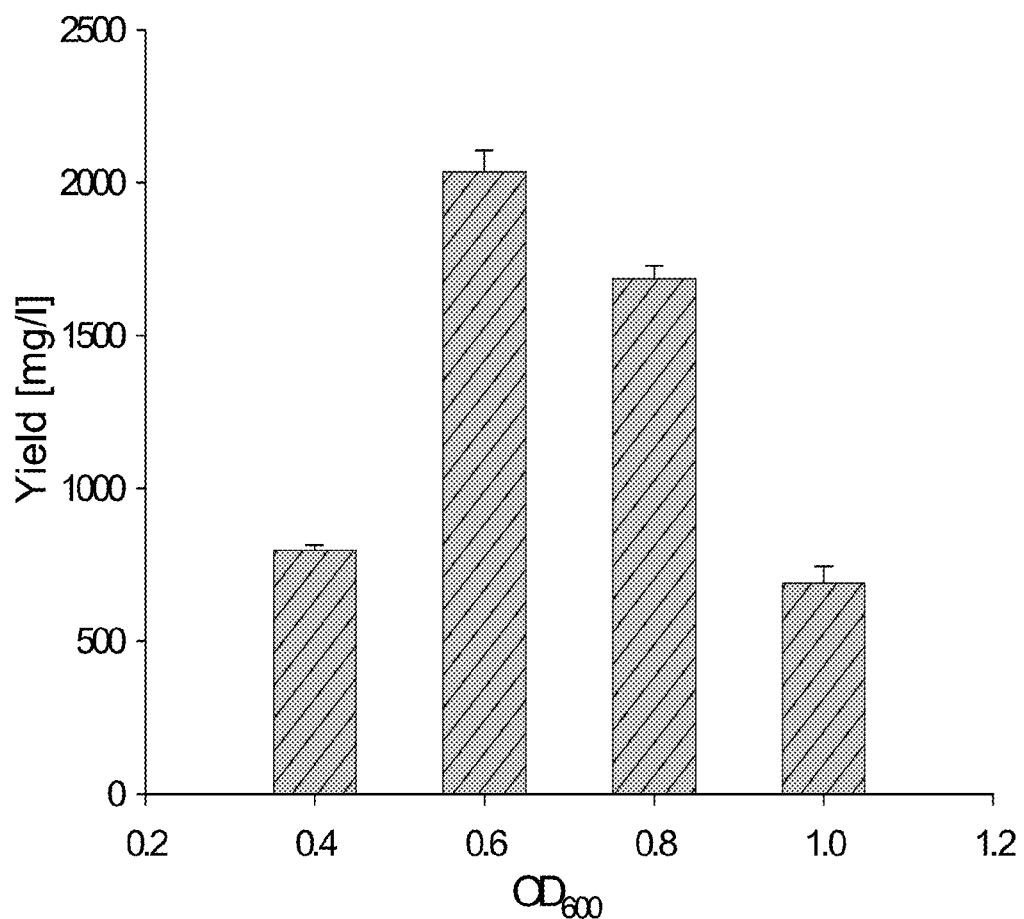

To optimize the production of indigoidine in *E. coli* BAP1, the fermentation conditions including the optimal OD600 value for IPTG induction, production temperature and fermentation time were investigated. *E. coli* BAP1/pJV6 was grown in four flasks containing 50 ml of LB medium supplemented with 50 µg/ml kanamycin at 37° C. The cultures were induced with 200 µM IPTG when the OD600 reached 0.4, 0.6, 0.8 and 1.0, respectively. The induced broths were maintained at 25° C. and 250 rpm for 13 hours, and then the yields of indigoidine were determined. As shown in FIG. 4B, induction of the fermentation broth at OD600 0.6 gave the best yield of the blue pigment.

Figure 4C:
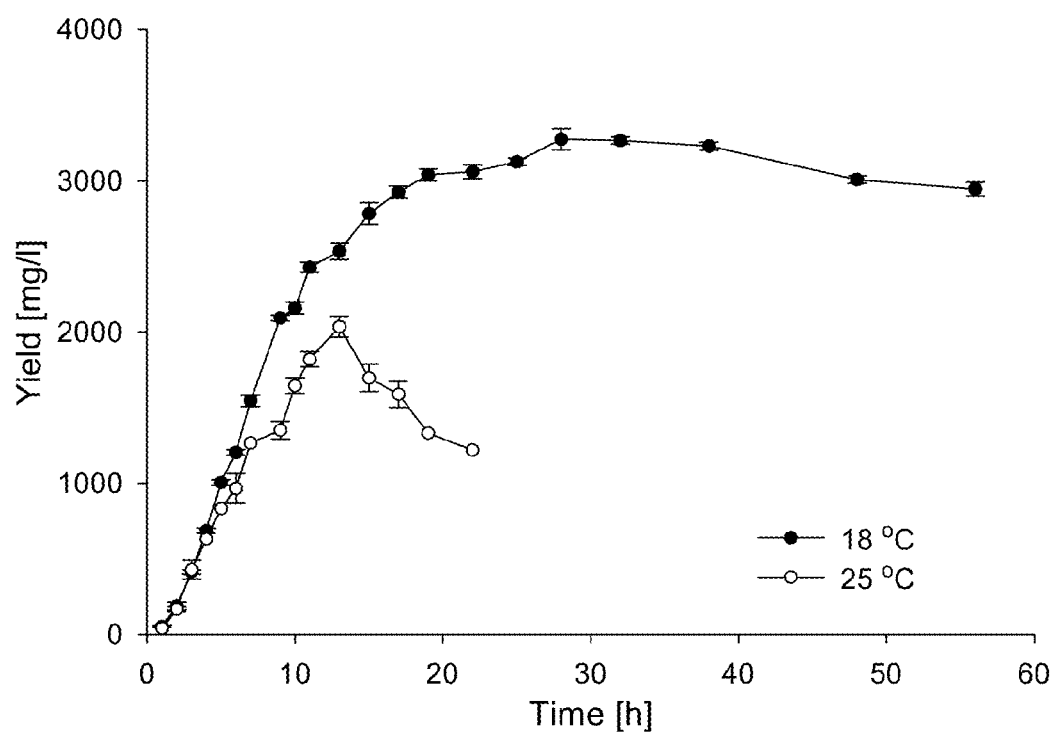

By way of example, and without limiting the invention, the present disclosure provides for four different fermentation temperatures including 18° C., 25° C., 30° C. and 37° C. Almost no indigoidine synthesis was detected at 30° C. and 37° C., which might be attributed to the thermal instability and oxidability of indigoidine. Time course analysis was conducted to monitor the production of indigoidine at 18° C. and 25° C. As shown in FIG. 4C, the yield of indigoidine reached the highest (1.73 g/l) after 13 hours of IPTG induction at 25° C., while at 18° C. the best yield (2.78 g/l) was achieved at 28 hours. The yield of indigoidine dropped after the maximal point, suggesting that long fermentation or storage time may result in the degradation of this blue pigment.

Example 14

Investigation of the Stability of Indigoidine

Figure 4D:
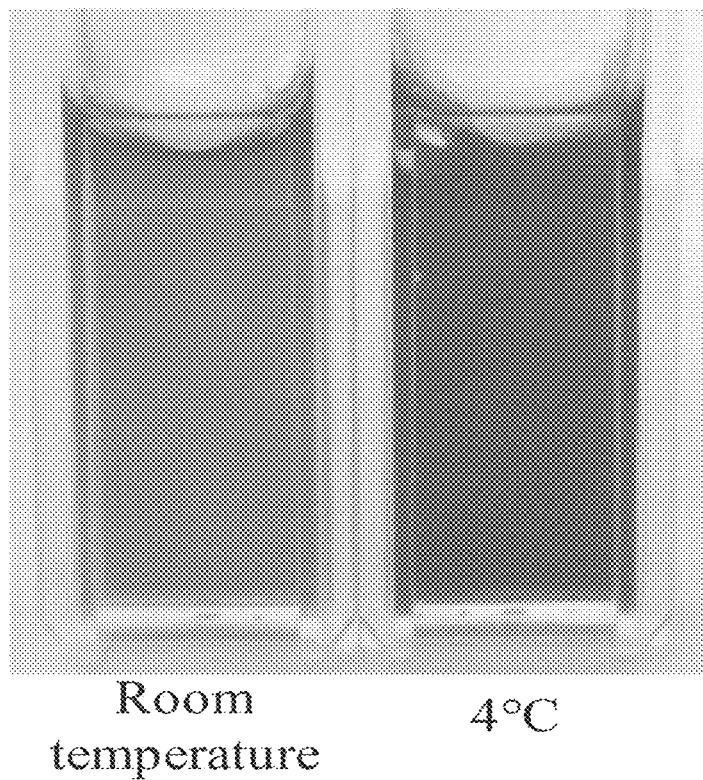

Some antioxidants, such as ascorbic acid, are commonly used to stabilize indigoidine. It was previously reported indigoidine pigment was very stable in tetrahydrofuran and did not fade for over 1 month, but indigoidine was hardly dissolved in the solvent in our experiments. Instead, we found that dimethyl sulfoxide is a good solvent to dissolve the pigment. However, even in dimethyl sulfoxide, the blue color of indigoidine can fade at room temperature over months. Degradation of indigoidine is much faster in the fermentation broth, as seen in the time course of indigoidine production at 25° C. (FIG. 4C). We also tested the stability of indigoidine in the fermentation broth at room temperature and 4° C. As shown in FIG. 4D, indigoidine in cell-free LB medium was more stable at 4° C., while the color of the pigment at room temperature faded significantly after 2 days.

Example 15

Co-Expression of Sc-IndB and Sc-IndC Increases Indigoidine Biosynthesis

Figure 5A:
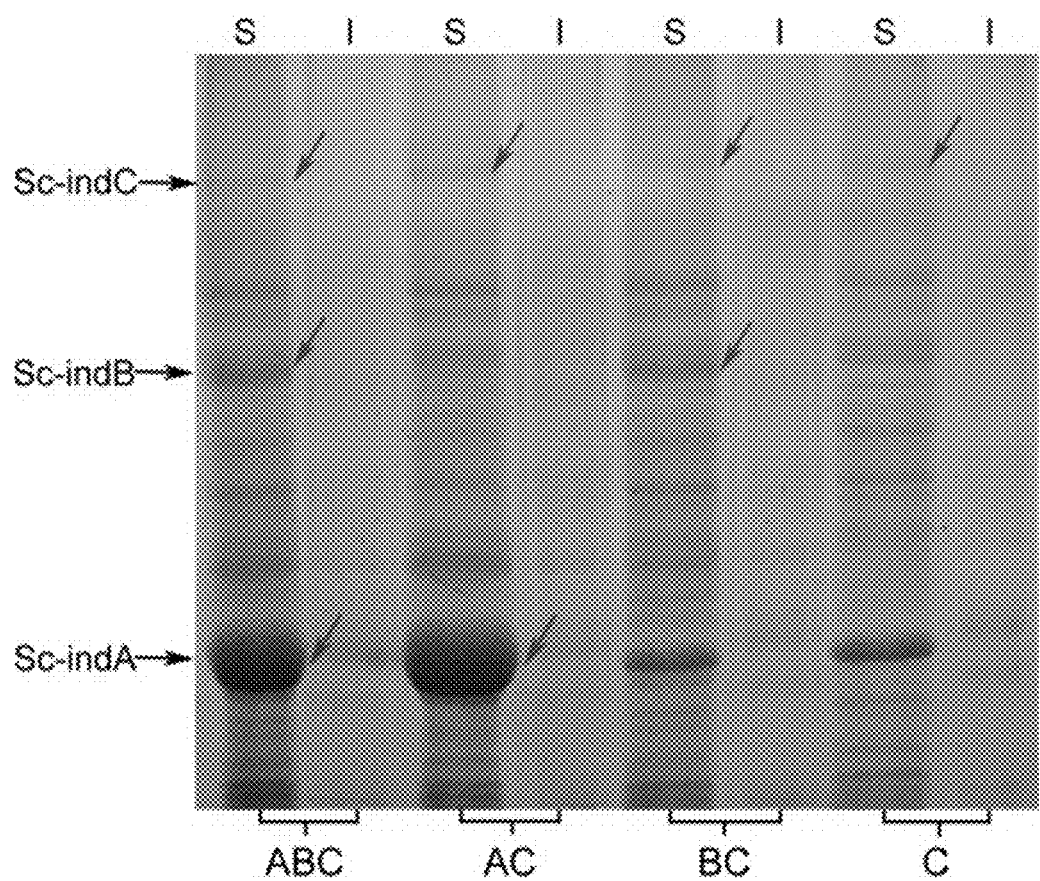
FIG. 5 depicts exemplary co-expression of Sc-IndC with Sc-IndA, with and without co-expression of Sc-IndB, in *E. coli* BAP1. (A) SDS-PAGE analysis of co-expression of Sc-IndA and/or Sc-IndB with Sc-IndC in *E. coli* BAP1. (B) The yield of indigoidine in *E. coli* BAP1 with or without co-expression of Sc-IndA and/or Sc-IndB. Experiments were performed in triplicate and presented as means±SD (n=3). C: Sc-IndC; AC: Sc-IndA and Sc-IndC; BC: Sc-IndB and Sc-IndC; ABC: Sc-IndA, Sc-IndB and Sc-IndC; S: soluble fraction; I: insoluble fraction.
Figure 5B:
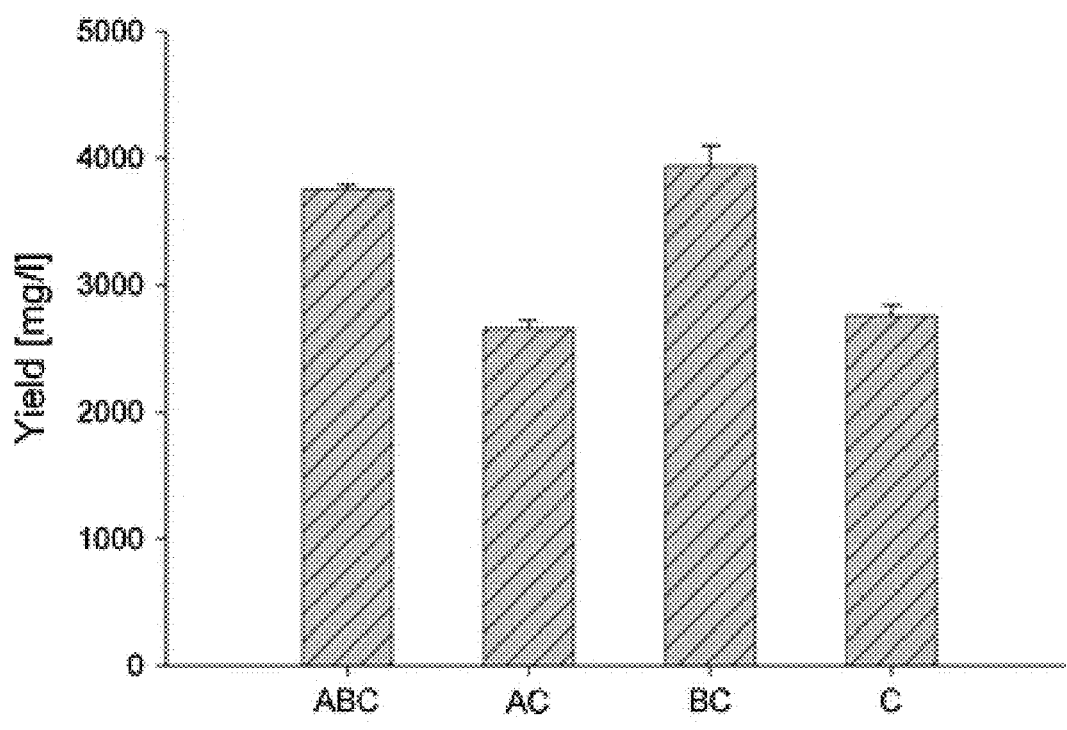

The Sc-indA and Sc-indB genes are present with Sc-indC in the same gene cluster in *S. chromofucus* ATCC 49982. To find out whether the Sc-indA and Sc-indB genes participate in indigoidine biosynthesis in *S. chromofucus* ATCC 49982, we constructed three plasmids using the pACYCDuet-1 vector, named pDY52, pDY53 and pDY54, which contain Sc-indA, Sc-indB, and Sc-indA and Sc-indB, respectively (Table 1). The plasmids were co-expressed in *E. coli* BAP1 with pJV6, separately. Both soluble and insoluble proteins of these strains were analyzed. SDS-PAGE analysis showed that Sc-IndA (33 kDa) and Sc-IndB (67 kDa) were co-expressed with Sc-IndC (150 kDa) in *E. coli* BAP1 cells at 18° C. (FIG. 5A). A comparison of the yield of indigoidine revealed that presence of Sc-IndB dramatically increased the production of indigoidine. As shown in FIG. 5B, *E. coli* BAP1/pJV6+ pDY53 that expressed both Sc-IndC and Sc-IndB gave the highest yield of 3.93 g/l at 18° C. after 28 hours. Co-expression of Sc-IndA with Sc-IndC did not show any improvement in the production of the pigment. Instead, a slight decrease in the yield was observed. This is likely due to the extremely high expression level of Sc-IndA, which might have influenced the expression of other proteins in the cells. Similarly, a slightly lower yield of indigoidine than that in *E. coli* BAP1/pJV6+pDY53 was observed when Sc-IndC was co-expressed with both Sc-IndB and Sc-IndA (FIG. 5B).

Example 16

Production of the Blue Pigment Indigoidine

Indigoidine is a blue pigment that has been found in several different bacteria such as *S. aureofaciens* and *E. chrysanthemi*. It is a powerful radical scavenger for the producing strains. This pigment can be easily extracted and quantified. More and more useful properties of indigoidine have been discovered and utilized in recent years. In addition to the antimicrobial activity, the bright blue color of this natural product makes it a useful and sensitive indicator in biochemical studies. For instance, indigoidine has recently been developed into a versatile and universal reporter for bacteria and mammalian cells. The indigoidine synthase BpsA has also been used as a reporter for rapid and flexible measurement of PPTase activity. This system can be used for discovery and characterization of PPTase inhibitors.

The present disclosure provides for a new indigoidine biosynthetic gene cluster from the pharmaceutically important strain *S. chromofucus* ATCC 49982 which produces the anticholesterol compound herboxidiene, further expanding the spectrum of indigoidine-producing strains. This gene cluster is silent under laboratory conditions as no pigment formation was observed in the host. We were able to reconstitute this indigoidine biosynthetic pathway in two different heterologous hosts, *S. coelicolor* CH999 and *E. coli* BAP1. Sc-IndC is a single module NRPS that contains four domains (A, Ox, T and TE). It is proposed that the A domain selects and activates the substrate L-glutamine and transfers the precursor to the PPTase-activated T domain. The TE domain may hydrolyze the amino acid from the enzyme and catalyzes the cyclization to form 5-aminopiperidine-2,6-dione, which can be further oxidized and dimerized by the Ox domain to yield indigoidine. Thus, activation of Sc-IndC is critical to the biosynthesis of the pigment. Although no heterologous PPTase was introduced into *S. coelicolor* CH999, the strain appears to be an effective host for indigoidine biosynthesis. An endogenous PPTase may contribute to the activation of the T domain of Sc-IndC. The yield difference between *S. coelicolor* CH999 and *E. coli* BAP1 may be due to the efficiency of the PPTase and expression level of Sc-IndC.

A number of factors can affect the yield of indigoidine, such as fermentation time and temperature. In some embodiments, temperature may range from 18° C. and 25° C. Preferably, the temperature may be about 18° C. Low temperatures may attribute to the stability of the modular indigoidine synthase Sc-IndC and the product indigoidine. The yield of indigoidine drops after the maximum point, when the degradation rate is larger than the biosynthesis rate. This was revealed by the time course analysis at both 18° C. and 25° C. No pigment formation was observed at 30° C. and 37° C., suggesting that the production process prefers a lower temperature. The present disclosure provides for OD600 values useful in determining a suitable time to induce Sc-IndC in order to synthesize indigoidine. It is shown herein that OD600 values at which expression of Sc-IndC was induced with IPTG may influence the yield of indigoidine. Induction at four different OD600 values demonstrated that 0.6 appeared to be the best. Under the optimal fermentation conditions, the yield of indigoidine reached 2.78 g/l in E. coli BAP1.

Indigoidine is water-insoluble. The pigment precipitates during the fermentation, which provides a convenient way to harvest it by centrifugation. This compound is also not soluble in most organic solvents, and dimethyl sulfoxide appeared to be a suitable solvent for this pigment. Degradation of indigoidine is fast and it can be stored longer at lower temperatures.

Genes encoding IndA- and IndB-like proteins are often found in indigoidine biosynthetic pathways from different strains. However, the functions of these two proteins are still unknown. While IndA (or IdgA) is a hypothetical protein, IndB (or IdgB) is a putative phosphatase. A previous study has shown that an idgA mutant of E. chrysanthemi RA3B was deficient in the pigment production, while the idgB mutant produced only low level of indigoidine, suggesting that both IdgA and IdgB are involved in indigoidine biosynthesis in E. chrysanthemi RA3B. IndA- and IndB-like enzymes were also found in some other natural product biosynthetic pathways. For instance, AlnA and AlnB, which are homologous to IdgA and IdgB, respectively, have been found to be involved in the formation and attachment of the dioxan moiety in alnumycin biosynthesis in Streptomyces sp. CM020 through a gene disruption approach.

The present disclosure provides for a heterologous expression approach to investigate the functions of Sc-IndA and Sc-IndB. Sc-IndA had no obvious effects on the production of the blue pigment, while co-expression of Sc-IndB with Sc-IndC increased the yield of indigoidine by 41.4%. Sc-IndB is a unique fusion protein that has been for the first time found in an indigoidine biosynthetic pathway. Its N-terminal portion is similar to IdgB and other homologues, which is a putative phosphatase belonging to the family of haloacid dehalogenase-like hydrolases. However, Sc-IndB is nearly three times the size of IdgB and its homologues, as it has a large C-terminal domain without a known function. Although the exact function of Sc-IndB is still unknown, it is clear from this work that this unusual enzyme is involved in the biosynthesis of the blue pigment. Co-expression of this protein with Sc-IndC provides an effective way to significantly improve the production of indigoidine.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

SEQUENCE LISTING

<160> NUMBER OF SEQ ID NOS: 4

<210> SEQ ID NO 1
<211> LENGTH: 1845
<212> TYPE: DNA
<213> ORGANISM: Streptomyces chromofuscus

<400> SEQUENCE: 1

```
atgttcgacc tggacggaac cctcgtcgac tcgccccggg cgatcgtgga ggcgttcgcc      60
gccgctttct gggcgatggg cctcgcgccc cgggacccgg cggacatccg ggccaccatc     120
ggcctgcccc tggagcaggc gttcgggaaa ctgctgggag taccgcagaa cgacccctcg     180
gtcgccgacg gcgtggcccg ctaccaggag gcgttccgca ccctcatcct ccccgcgcc      240 cactcgctgg tcttccccgg cgtccccgag ggcctcgccg aactgcgccg tcacggtgtc     300
gtggtgacgg tggccacgag caagttccat gccagcgccg atgccctgct caccgccgcg     360
ggcctgcgcg accacgtcac cacactggtc ggcgccgacg acgtcacccg tcccaagccg     420 cacccccgagt cggggctgct gatcctcgga gagctcggcg cccggcccga gcacgccgtg     480
atggtcggcg acaccaccca cgacctgaag atggccgcgg cggccggcct ggcgtccgtg     540
gcggtcacct acggggtcca cgagcgggcg gagctggaga cggcctcacc gacacacgtc     600
gccgacacgt tcgcccaggc cgtggagcag atcctcgccg tcctgccggc cgacggcgga     660
ccggaggaca ccggcaccgt cgagagcctc ctggacgaca gcacgtacca catcgagttc     720
aacggccacc tcaccaacca catcaagcac gccgtcgtcg ccctcgccgg cctcggtgtc     780
```

```
gaccccggcc ggatcaaggc gtaccacgac aactacatcg ccctcacgcc gtacggctgc    840
cgcgtcgagc cggccagacc tccccagcga ctgatcgacg acggcaactg gctcgaacac    900
ctcggccggc gcgaggactt cgccgcgtac tgcgcgttct tcgaccggcg cgaacgggaa    960
ctgggcatgg cgggtctgct acggcagtac gtaccgcgcc tgctcgcggg ctgggccggt   1020
gcgctccagc acgcgaccat ccacctgggc tgggccctgg acgccggcaa ccgccgcatg   1080
gccatcgagg gcatcgccta cctggccttc gcgtacgtcg actgccatcc cgaacgcgcc   1140
gtgccctcgg aagcgcccgg caccgacaag cccggggact cgctgctgag catcgcccgc   1200
cactgggagg agaacgggcc ccggctcggc gcctgggtcg aggacctggt cggaaccacg   1260
agcgccgaca tccaccccga actcctgcgg tccgggctgc agtaccggat cgcccggatg   1320
ctcggcgagg gccatccgct gatgtacggg acaccctcct ggatcgccgc gcaggacccc   1380
gacaccagtt gggagcagct cgcctacctc gtcaccgttc tctacctgac cgaaccggga   1440
gacttcctcc tgctgcacct ggtcaccgcg ctccacgcga tgcgtcacat cgcggacgcc   1500
ctccccgccg agcagcagcg gcgagcggtc gcgtgctact ggaccggcat cctcggtgtg   1560
ctcttctccc ggggccactt cgtcgcccct tcgaagctga ccgcgatcga cagcctcttc   1620
gacaccgccc tggacgacct ggacgacccg cgctgggccc gggagtggga ctggcacatc   1680
gcgcgggccg tggaggagga agaggagcac aacgccaagc tcgtctacgt gatgcgcgag   1740
ttgtggcgcg gctcgggcgg caggtccgtg taccgcgtcg ccgccgggca gttcaccacc   1800
accccggagc tccccgccac cttcgagcag ccccccggtcg actga                  1845
```

<210> SEQ ID NO 2
<211> LENGTH: 614
<212> TYPE: PRT
<213> ORGANISM: Streptomyces chromofuscus

<400> SEQUENCE: 2

```
Met Phe Asp Leu Asp Gly Thr Leu Val Asp Ser Pro Arg Ala Ile Val
1               5                   10                  15

Glu Ala Phe Ala Ala Ala Phe Trp Ala Met Gly Leu Ala Pro Arg Asp
            20                  25                  30

Pro Ala Asp Ile Arg Ala Thr Ile Gly Leu Pro Leu Glu Gln Ala Phe
        35                  40                  45

Gly Lys Leu Leu Gly Val Pro Gln Asn Asp Pro Ser Val Ala Asp Gly
    50                  55                  60

Val Ala Arg Tyr Gln Glu Ala Phe Arg Thr Leu Ile Leu Pro Arg Ala
65                  70                  75                  80

His Ser Leu Val Phe Pro Gly Val Pro Glu Gly Leu Ala Glu Leu Arg
                85                  90                  95

Arg His Gly Val Val Thr Val Ala Thr Ser Lys Phe His Ala Ser
            100                 105                 110

Ala Asp Ala Leu Leu Thr Ala Ala Gly Leu Arg Asp His Val Thr Thr
        115                 120                 125

Leu Val Gly Ala Asp Asp Val Thr Arg Pro Lys Pro His Pro Glu Ser
    130                 135                 140

Gly Leu Leu Ile Leu Gly Glu Leu Gly Ala Arg Pro Glu His Ala Val
145                 150                 155                 160

Met Val Gly Asp Thr Thr His Asp Leu Lys Met Ala Ala Ala Gly
                165                 170                 175

Leu Ala Ser Val Ala Val Thr Tyr Gly Val His Glu Arg Ala Glu Leu
            180                 185                 190
```

```
Glu Thr Ala Ser Pro Thr His Val Ala Asp Thr Phe Ala Gln Ala Val
            195                 200                 205

Glu Gln Ile Leu Ala Val Leu Pro Ala Asp Gly Pro Glu Asp Thr
210                 215                 220

Gly Thr Val Glu Ser Leu Leu Asp Asp Ser Thr Tyr His Ile Glu Phe
225                 230                 235                 240

Asn Gly His Leu Thr Asn His Ile Lys His Ala Val Val Ala Leu Ala
            245                 250                 255

Gly Leu Gly Val Asp Pro Gly Arg Ile Lys Ala Tyr His Asp Asn Tyr
            260                 265                 270

Ile Ala Leu Thr Pro Tyr Gly Cys Arg Val Glu Pro Ala Arg Pro Pro
            275                 280                 285

Gln Arg Leu Ile Asp Asp Gly Asn Trp Leu Glu His Leu Gly Arg Arg
290                 295                 300

Glu Asp Phe Ala Ala Tyr Cys Ala Phe Phe Asp Arg Arg Glu Arg Glu
305                 310                 315                 320

Leu Gly Met Ala Gly Leu Leu Arg Gln Tyr Val Pro Arg Leu Leu Ala
            325                 330                 335

Gly Trp Ala Gly Ala Leu Gln His Ala Thr Ile His Leu Gly Trp Ala
            340                 345                 350

Leu Asp Ala Gly Asn Arg Arg Met Ala Ile Glu Gly Ile Ala Tyr Leu
            355                 360                 365

Ala Phe Ala Tyr Val Asp Cys His Pro Glu Arg Ala Val Pro Ser Glu
            370                 375                 380

Ala Pro Gly Thr Asp Lys Pro Gly Asp Ser Leu Leu Ser Ile Ala Arg
385                 390                 395                 400

His Trp Glu Glu Asn Gly Pro Arg Leu Gly Ala Trp Val Glu Asp Leu
            405                 410                 415

Val Gly Thr Thr Ser Ala Asp Ile His Pro Glu Leu Leu Arg Ser Gly
            420                 425                 430

Leu Gln Tyr Arg Ile Ala Arg Met Leu Gly Glu Gly His Pro Leu Met
            435                 440                 445

Tyr Gly Thr Pro Ser Trp Ile Ala Ala Gln Asp Pro Asp Thr Ser Trp
            450                 455                 460

Glu Gln Leu Ala Tyr Leu Val Thr Val Leu Tyr Leu Thr Glu Pro Gly
465                 470                 475                 480

Asp Phe Leu Leu Leu His Leu Val Thr Ala Leu His Ala Met Arg His
            485                 490                 495

Ile Ala Asp Ala Leu Pro Ala Glu Gln Gln Arg Arg Ala Val Ala Cys
            500                 505                 510

Tyr Trp Thr Gly Ile Leu Gly Val Leu Phe Ser Arg Gly His Phe Val
            515                 520                 525

Ala Pro Ser Lys Leu Thr Ala Ile Asp Ser Leu Phe Asp Thr Ala Leu
530                 535                 540

Asp Asp Leu Asp Asp Pro Arg Trp Ala Arg Glu Trp Asp Trp His Ile
545                 550                 555                 560

Ala Arg Ala Val Glu Glu Glu Glu His Asn Ala Lys Leu Val Tyr
            565                 570                 575

Val Met Arg Glu Leu Trp Arg Gly Ser Gly Arg Ser Val Tyr Arg
            580                 585                 590

Val Ala Ala Gly Gln Phe Thr Thr Pro Glu Leu Pro Ala Thr Phe
            595                 600                 605
```

Glu Gln Pro Pro Val Asp
    610

<210> SEQ ID NO 3
<211> LENGTH: 4134
<212> TYPE: DNA
<213> ORGANISM: Streptomyces chromofuscus

<400> SEQUENCE: 3

| | | | | |
|---|---|---|---|---|
| atgagcgtag agaccatccc ctgctctcgt cgtgccgccc tcggcctgcc cggcctgttg | 60 |
| cgcgaacgag ctcgggccac ccccgaccgg acagccgccg ttcacgagca ccagagcctg | 120 |
| acattcgccc agttgacgga ggacagctcc catgtgggag cgctcctgcg gcaggccggg | 180 |
| gtgggccggg acagccgggt cggcgtgttc atggagccgt cgctcgacct gctgacgggc | 240 |
| gtctggggaa tcctgtgggc cggcggatgc tacgtaccgt tgtccccgga atacccggag | 300 |
| gagaggatcg cgtacatgct ggcggacgcc ggcgtcgaca tcgttctcac ccaggaattc | 360 |
| cttcggtcga cccttcagga gctcgctccg gccggggtcg ttgttctcac tctcgacgag | 420 |
| atgttgagga cggcggagag ggacggcagt gcattcggcc ggccggagcc cgaggtacgg | 480 |
| cccgacgatc tcgcctatgt catctacacc tccggcagca ccggaaagcc aaaaggtgtg | 540 |
| atggtcgagc accggagcat cgtgagtcaa atgcgatggc tgcacgacga gtgcggtatc | 600 |
| gatgaaaacg aaataatact gcagaagacc ccgatgagtt tcgatgccgc gcagtgggaa | 660 |
| ttactcgccc tcgcctgcgg cagcaccgtg gtgatgggat cctccggtat ctaccgcgac | 720 |
| cccgaggcga tcatctccac cgtccaacgg cacggcgtga ccaccctcca gtgcgtgccc | 780 |
| accctgctcc aggcgctcct ggacaccgag aagttccccg actgcgggac cctgcgccgc | 840 |
| atcttcagcg ggggcgaggc gctctcccgg agtctcgccg cgcagtgcct ggacaccatg | 900 |
| ccgggggccc gtctggtcaa cctctacggc cccaccgagt gcaccatcaa cgcctcgtcc | 960 |
| ttcgtggtgg accgcgccgc gctggaggac gggccgctcg tcatgccgat cggcaccccc | 1020 |
| gtgcacgaca cctccctgca cgtcctgaga ccggacggtg cgccggtctc cgccggggag | 1080 |
| atcggcgaac tgtacatcgg cggtgtgcag gtggcccgcg gctacctcgg ccgcccggac | 1140 |
| ctgaccggcg accggttcat ggccgacccc ttctccgacg cgcccggctc ccgcctctac | 1200 |
| cggaccggcg acctcgccca tgtcaacgcg gacggcacgg tgcagttcgt cggacgcgcc | 1260 |
| gacaaccagg tcaagctgcg cggctaccgg gtcgaactgg acgagatacg ccagaccgtc | 1320 |
| gagacgcacg actgggtccg cgccgcggcc gtcctgctcc gcgacgacgc caccacgggc | 1380 |
| ttccagaacc tcgtcgcctt cgtcgagctc aaccccaagg aagccgccct gatgaccagg | 1440 |
| ggcaaccacg gctcccacca ccagtccaag gccagccggc tccaggtcag ggcccaactg | 1500 |
| gcccaccccg gctgccgcga cgacgccgat ctggccggcc gggcggccat cgacctgccc | 1560 |
| ggcgccgagg ccaccccccgg gcagcgggcc ctcgccttct cccgcaagac gtaccgcttc | 1620 |
| tacgagggct ccccggtgac ccgggacgac atcctgcacc tgctcggccc ccgtccccgg | 1680 |
| ccgcggccgt ccgcccgtac ctccgacatc gtcggccgcg acgaactcgg tacgatcctg | 1740 |
| cggaacttcg gccgtcacct cagcgaccag aggctgctgc caagtacgcg ctacgcctca | 1800 |
| cccggctccc tgtacgcgac gcagttgtac gtcgagatcg gcggcgggca cgacgttccc | 1860 |
| gcgggcctgt actactacca cccgctccac caccggctgg tgctcgtcgg cccggcctcc | 1920 |
| gagaccgaga cctccccggt acggatccac ttcctcggca gcacggcgc catcgagccg | 1980 |
| gtctaccgca caacgtccg cgaggtcctg gagatcgagg cgggccacat ggtcggcctg | 2040 |

| | |
|---|---|
| ttcgaggagg tgctgccggc ccacggcctg cgcatcgccg cggccgcgta ccaaccggcc | 2100 |
| gtcagacacc gtctcgactg cgcgccggag gaccactacc tgggcagctt cgacctcctt | 2160 |
| ccgcaggcgc ggggcgcgtc cgaggacacc gacaccctcg acatctacgt ccaggcccac | 2220 |
| tccacccgga tcgagggcct gccgccgggt cagtaccggt acaccggcgc cggcctcgtc | 2280 |
| cgtatcggcg acgacgtgat cctcaagaag cacgtcatcg ccatcaacca gcgggtctac | 2340 |
| gagcgttccg acttcggtat cagcctggtc gccaccggtt ccgcctcctg gcggcgctat | 2400 |
| ctcgacctgg gtcgcgggct ccagcgcctc cagatgaacg acctgcacct cggcttcatg | 2460 |
| tcctcgggct acagctcgaa gtccggtaac gacctgccgt cggccaagcg gctgggccgg | 2520 |
| atcctcgccg acggcgggtt gcccgccgga ccgtcgtact tctgcgtcgg cgggcgtgtc | 2580 |
| agcgacgcgc agtggcgcgg cgaggacatg aaggaggacg tggtccacat gcaggggccc | 2640 |
| gccgagctga tcaaggagga tctggccgcg ctgctgcccc gctacatgct gcccaaccgg | 2700 |
| atcgtcgtcc tggaccggct gccccagacc gccaacggca agatcgacct gaaggccctg | 2760 |
| cagaccactc aggaagccca actgaccgtc ggcgaacgcg ctttcatggc tccgcgcacc | 2820 |
| ccgctggagc ggcggatccg cgacatctgg caggcggtgc tcaagcggga ccaggtctcc | 2880 |
| gtcaccgacg acttcttcga actgggcggg aactccctgc tcgccgtggc tctggtcagc | 2940 |
| cgcctgaacg cggacttcgg cggcgcgatc cccctgcaga tcctgttcga ggcccccacc | 3000 |
| gtggagaggc tcgccgcggc cctggaggcc acgtcacccc ggcccgcctc ccgtctggtg | 3060 |
| ccgctccagc ccgagggcag gggcacccc g ctgtactgct ggccgggcct cggcggctac | 3120 |
| cccatgaacc tgcgtccgct ggccgcggcc ctgggcacgg agcggcccgt ccacggggtc | 3180 |
| caggcccacg gcatcaaccc cggcgagttc ccctacgacg atgtccgtgc catggccgcc | 3240 |
| gccgatgtcg aggcgatccg ggagatccag ccccacggcc cgtacctgct gtgcggatac | 3300 |
| tccttcggcg cccgggtcgc cttcgaggcc gcgcgccagt ggaacaggc gggcgagcag | 3360 |
| gtggagcagt tgttcctcgt ggctcccggc cagccgcggc tgcgccccga ggacgccgtc | 3420 |
| ggcgcgaccg gccgggcgga cttcacggac cgcgccttcc tcgccctgct cttctccgtc | 3480 |
| ttcgccggca cgctcagcgg cccgcgactg gaccagtgcc tgcgcaccgt caccgacgag | 3540 |
| gacggcttcg tcgcattcgt caccgcgtcc ttcccgggac tcggcgagga gctggtacgg | 3600 |
| gcggtcaccg ggatcgtacg ccgcacgtac tccctcacct acgagttcca cgagctgcgc | 3660 |
| ggacgccgtc tcgacgcgcc cgtgaccctg gtcagggcca ccgacgacaa ctactccttc | 3720 |
| atcgagcacg agggcgggta ctccgcccgg ccgcccgccg tccaccaact gcggtccggc | 3780 |
| cactacgaac tgctgcgcga ccgcatgtcg gccccggctcg ccgctgtcct caacgaccgg | 3840 |
| ctgtccgccg gtcccagcac gtccccccgt cacagccagc cggcgcaagc cacggtccag | 3900 |
| gaggtcggag tgccccacat caacatcaag cacttcccgg tgtcgatcac cgaggagaag | 3960 |
| gagctggagc tggtcgccgc ggtcaccacg gccgtgcgca acgccttcgg ctgcaccgag | 4020 |
| gaggtcgtct ccatcgccct ggagcccgtc gcccaggagg tgtggaacga gcgggtctac | 4080 |
| atccccgaga tcgtcgcccg gcaggagttg ctgcgcaaga cgcccaacta ctga | 4134 |

<210> SEQ ID NO 4
<211> LENGTH: 1377
<212> TYPE: PRT
<213> ORGANISM: Streptomyces chromofuscus

<400> SEQUENCE: 4

Met Ser Val Glu Thr Ile Pro Cys Ser Arg Arg Ala Ala Leu Gly Leu

-continued

```
  1               5                  10                 15
Pro Gly Leu Leu Arg Glu Arg Ala Arg Ala Thr Pro Asp Arg Thr Ala
              20                 25                 30
Ala Val His Glu His Gln Ser Leu Thr Phe Ala Gln Leu Thr Glu Asp
              35                 40                 45
Ser Ser His Val Gly Ala Leu Leu Arg Gln Ala Gly Val Gly Arg Asp
              50                 55                 60
Ser Arg Val Gly Val Phe Met Glu Pro Ser Leu Asp Leu Leu Thr Gly
 65                70                 75                 80
Val Trp Gly Ile Leu Trp Ala Gly Gly Cys Tyr Val Pro Leu Ser Pro
                  85                 90                 95
Glu Tyr Pro Glu Glu Arg Ile Ala Tyr Met Leu Ala Asp Ala Gly Val
             100                105                110
Asp Ile Val Leu Thr Gln Glu Phe Leu Arg Ser Thr Leu Gln Glu Leu
             115                120                125
Ala Pro Ala Gly Val Val Leu Thr Leu Asp Glu Met Leu Arg Thr
             130                135                140
Ala Glu Arg Asp Gly Ser Ala Phe Gly Arg Pro Glu Pro Glu Val Arg
145                150                155                160
Pro Asp Asp Leu Ala Tyr Val Ile Tyr Thr Ser Gly Ser Thr Gly Lys
                 165                170                175
Pro Lys Gly Val Met Val Glu His Arg Ser Ile Val Ser Gln Met Arg
             180                185                190
Trp Leu His Asp Glu Cys Gly Ile Asp Glu Asn Glu Ile Ile Leu Gln
             195                200                205
Lys Thr Pro Met Ser Phe Asp Ala Ala Gln Trp Glu Leu Leu Ala Leu
             210                215                220
Ala Cys Gly Ser Thr Val Val Met Gly Ser Ser Gly Ile Tyr Arg Asp
225                230                235                240
Pro Glu Ala Ile Ile Ser Thr Val Gln Arg His Gly Val Thr Thr Leu
                 245                250                255
Gln Cys Val Pro Thr Leu Leu Gln Ala Leu Leu Asp Thr Glu Lys Phe
             260                265                270
Pro Asp Cys Gly Thr Leu Arg Arg Ile Phe Ser Gly Gly Glu Ala Leu
             275                280                285
Ser Arg Ser Leu Ala Ala Gln Cys Leu Asp Thr Met Pro Gly Ala Arg
             290                295                300
Leu Val Asn Leu Tyr Gly Pro Thr Glu Cys Thr Ile Asn Ala Ser Ser
305                310                315                320
Phe Val Val Asp Arg Ala Ala Leu Glu Asp Gly Pro Leu Val Met Pro
                 325                330                335
Ile Gly Thr Pro Val His Asp Thr Ser Leu His Val Leu Arg Pro Asp
             340                345                350
Gly Ala Pro Val Ser Ala Gly Glu Ile Gly Glu Leu Tyr Ile Gly Gly
             355                360                365
Val Gln Val Ala Arg Gly Tyr Leu Gly Arg Pro Asp Leu Thr Gly Asp
             370                375                380
Arg Phe Met Ala Asp Pro Phe Ser Asp Ala Pro Gly Ser Arg Leu Tyr
385                390                395                400
Arg Thr Gly Asp Leu Ala His Val Asn Ala Asp Gly Thr Val Gln Phe
                 405                410                415
Val Gly Arg Ala Asp Asn Gln Val Lys Leu Arg Gly Tyr Arg Val Glu
             420                425                430
```

```
Leu Asp Glu Ile Arg Gln Thr Val Glu Thr His Asp Trp Arg Ala
            435                 440                 445
Ala Ala Val Leu Leu Arg Asp Asp Ala Thr Thr Gly Phe Gln Asn Leu
450                 455                 460
Val Ala Phe Val Glu Leu Asn Pro Lys Glu Ala Ala Leu Met Asp Gln
465                 470                 475                 480
Gly Asn His Gly Ser His His Gln Ser Lys Ala Ser Arg Leu Gln Val
                485                 490                 495
Arg Ala Gln Leu Ala His Pro Gly Cys Arg Asp Asp Ala Asp Leu Ala
            500                 505                 510
Gly Arg Ala Ala Ile Asp Leu Pro Gly Ala Glu Ala Thr Pro Gly Gln
            515                 520                 525
Arg Ala Leu Ala Phe Ser Arg Lys Thr Tyr Arg Phe Tyr Glu Gly Ser
            530                 535                 540
Pro Val Thr Arg Asp Asp Ile Leu His Leu Leu Gly Pro Arg Pro Arg
545                 550                 555                 560
Pro Arg Pro Ser Ala Arg Thr Ser Asp Ile Val Gly Arg Asp Glu Leu
                565                 570                 575
Gly Thr Ile Leu Arg Asn Phe Gly Arg His Leu Ser Asp Gln Arg Leu
            580                 585                 590
Leu Pro Lys Tyr Ala Tyr Ala Ser Pro Gly Ser Leu Tyr Ala Thr Gln
            595                 600                 605
Leu Tyr Val Glu Ile Gly Gly His Asp Val Pro Ala Gly Leu Tyr
            610                 615                 620
Tyr Tyr His Pro Leu His His Arg Leu Val Leu Val Gly Pro Ala Ser
625                 630                 635                 640
Glu Thr Glu Thr Ser Pro Val Arg Ile His Phe Leu Gly Lys His Gly
                645                 650                 655
Ala Ile Glu Pro Val Tyr Arg Asn Asn Val Arg Glu Val Leu Glu Ile
            660                 665                 670
Glu Ala Gly His Met Val Gly Leu Phe Glu Glu Val Leu Pro Ala His
            675                 680                 685
Gly Leu Arg Ile Ala Ala Ala Tyr Gln Pro Ala Val Arg His Arg
            690                 695                 700
Leu Asp Cys Ala Pro Glu Asp His Tyr Leu Gly Ser Phe Asp Leu Leu
705                 710                 715                 720
Pro Gln Ala Arg Gly Ala Ser Glu Asp Thr Asp Thr Leu Asp Ile Tyr
                725                 730                 735
Val Gln Ala His Ser Thr Arg Ile Glu Gly Leu Pro Pro Gly Gln Tyr
            740                 745                 750
Arg Tyr Thr Gly Ala Gly Leu Val Arg Ile Gly Asp Asp Val Ile Leu
            755                 760                 765
Lys Lys His Val Ile Ala Ile Asn Gln Arg Val Tyr Glu Arg Ser Asp
770                 775                 780
Phe Gly Ile Ser Leu Val Ala Thr Gly Ser Ala Ser Trp Arg Arg Tyr
785                 790                 795                 800
Leu Asp Leu Gly Arg Gly Leu Gln Arg Leu Gln Met Asn Asp Leu His
                805                 810                 815
Leu Gly Phe Met Ser Ser Gly Tyr Ser Ser Lys Ser Gly Asn Asp Leu
            820                 825                 830
Pro Ser Ala Lys Arg Leu Gly Arg Ile Leu Ala Asp Gly Gly Leu Pro
            835                 840                 845
```

```
Ala Gly Pro Ser Tyr Phe Cys Val Gly Gly Arg Val Ser Asp Ala Gln
850                 855                 860

Trp Arg Gly Glu Asp Met Lys Glu Asp Val Val His Met Gln Gly Pro
865                 870                 875                 880

Ala Glu Leu Ile Lys Glu Asp Leu Ala Ala Leu Leu Pro Arg Tyr Met
                885                 890                 895

Leu Pro Asn Arg Ile Val Val Leu Asp Arg Leu Pro Gln Thr Ala Asn
            900                 905                 910

Gly Lys Ile Asp Leu Lys Ala Leu Gln Thr Thr Gln Glu Ala Gln Leu
        915                 920                 925

Thr Val Gly Glu Arg Ala Phe Met Ala Pro Arg Thr Pro Leu Glu Arg
930                 935                 940

Arg Ile Arg Asp Ile Trp Gln Ala Val Leu Lys Arg Asp Gln Val Ser
945                 950                 955                 960

Val Thr Asp Asp Phe Phe Glu Leu Gly Gly Asn Ser Leu Leu Ala Val
                965                 970                 975

Ala Leu Val Ser Arg Leu Asn Ala Asp Phe Gly Gly Ala Ile Pro Leu
            980                 985                 990

Gln Ile Leu Phe Glu Ala Pro Thr  Val Glu Arg Leu Ala  Ala Ala Leu
        995                 1000                1005

Glu Ala  Thr Ser Pro Arg Pro  Ala Ser Arg Leu Val  Pro Leu Gln
1010                 1015                1020

Pro Glu  Gly Arg Gly Thr Pro  Leu Tyr Cys Trp Pro  Gly Leu Gly
1025                 1030                1035

Gly Tyr  Pro Met Asn Leu Arg  Pro Leu Ala Ala Ala  Leu Gly Thr
1040                 1045                1050

Glu Arg  Pro Val His Gly Val  Gln Ala His Gly Ile  Asn Pro Gly
1055                 1060                1065

Glu Phe  Pro Tyr Asp Asp Val  Arg Ala Met Ala Ala  Ala Asp Val
1070                 1075                1080

Glu Ala  Ile Arg Glu Ile Gln  Pro His Gly Pro Tyr  Leu Leu Cys
1085                 1090                1095

Gly Tyr  Ser Phe Gly Ala Arg  Val Ala Phe Glu Ala  Ala Arg Gln
1100                 1105                1110

Leu Glu  Gln Ala Gly Glu Gln  Val Glu Gln Leu Phe  Leu Val Ala
1115                 1120                1125

Pro Gly  Gln Pro Arg Leu Arg  Pro Glu Asp Ala Val  Gly Ala Thr
1130                 1135                1140

Gly Arg  Ala Asp Phe Thr Asp  Arg Ala Phe Leu Ala  Leu Leu Phe
1145                 1150                1155

Ser Val  Phe Ala Gly Thr Leu  Ser Gly Pro Arg Leu  Asp Gln Cys
1160                 1165                1170

Leu Arg  Thr Val Thr Asp Glu  Asp Gly Phe Val Ala  Phe Val Thr
1175                 1180                1185

Ala Ser  Phe Pro Gly Leu Gly  Glu Glu Leu Val Arg  Ala Val Thr
1190                 1195                1200

Gly Ile  Val Arg Arg Thr Tyr  Ser Leu Thr Tyr Glu  Phe His Glu
1205                 1210                1215

Leu Arg  Gly Arg Arg Leu Asp  Ala Pro Val Thr Leu  Val Arg Ala
1220                 1225                1230

Thr Asp  Asp Asn Tyr Ser Phe  Ile Glu His Glu Gly  Gly Tyr Ser
1235                 1240                1245

Ala Arg  Pro Pro Ala Val His  Gln Leu Arg Ser Gly  His Tyr Glu
```

-continued

|  | 1250 |  |  |  | 1255 |  |  |  | 1260 |  |  |
|---|---|---|---|---|---|---|---|---|---|---|---|
| Leu | Leu<br>1265 | Arg | Glu | Pro | His | Val<br>1270 | Ala | Arg | Leu | Ala | Ala<br>1275 | Val | Leu | Asn |
| Asp | Arg<br>1280 | Leu | Ser | Ala | Gly | Pro<br>1285 | Ser | Thr | Ser | Pro | Arg<br>1290 | His | Ser | Gln |
| Pro | Ala<br>1295 | Gln | Ala | Thr | Val | Gln<br>1300 | Glu | Val | Gly | Val | Pro<br>1305 | His | Ile | Asn |
| Ile | Lys<br>1310 | His | Phe | Pro | Val | Ser<br>1315 | Ile | Thr | Glu | Glu | Lys<br>1320 | Glu | Leu | Glu |
| Leu | Val<br>1325 | Ala | Ala | Val | Thr | Thr<br>1330 | Ala | Val | Arg | Asn | Ala<br>1335 | Phe | Gly | Cys |
| Thr | Glu<br>1340 | Glu | Val | Val | Ser | Ile<br>1345 | Ala | Leu | Glu | Pro | Val<br>1350 | Ala | Gln | Glu |
| Val | Trp<br>1355 | Asn | Glu | Arg | Val | Tyr<br>1360 | Ile | Pro | Glu | Ile | Val<br>1365 | Ala | Arg | Gln |
| Glu | Leu<br>1370 | Leu | Arg | Lys | Thr | Pro<br>1375 | Asn | Tyr |  |  |  |  |  |  |

What is claimed is:

1. An expression system for the production of blue pigment indigoidine, comprising:
   (i) a heterologous host cell,
   (ii) a DNA sequence encoding a Sc-IndB protein and having at least 85% identity to the amino acid sequence set forth in SEQ ID NO:2,
   (iii) a DNA sequence encoding a Sc-IndC protein and having at least 85% identity to the amino acid sequence set forth in SEQ ID NO:4,
   wherein the system is configured for the co-expression of the Sc-IndB and Sc-IndC.

2. The expression system of claim 1, wherein the DNA sequences encoding the Sc-IndB and Sc-IndC are provided on at least one vector.

3. The expression system of claim 2, wherein the DNA sequences are provided on a single vector.

4. The expression system of claim 1, wherein at least one of the DNA sequences encoding the Sc-IndB and Sc-IndC are integrated into the genome of the heterologous host genome.

5. The expression system of claim 1, further comprising a *Bacillus subtilis*-derived sfp gene.

6. The expression system of claim 1, further comprising a 4'-phosphopantetheinyl transferase (PPTase).

7. The expression system of claim 6, wherein the PPTase is an endogenous host PPTase.

8. The expression system of claim 6, wherein the PPTase is an exogenous PPTase.

9. The expression system of claim 1, wherein the DNA sequences encoding the Sc-IndB and Sc-IndC are operatively linked to at least one promoter.

10. The expression system of claim 9, wherein the DNA sequences encoding the Sc-IndB and Sc-IndC are operatively linked to a single promoter.

11. The expression system of claim 1, wherein the DNA sequence encoding the Sc-IndB protein is a sequence at least 85% identical to the sequence set forth in SEQ ID NO:1.

12. The expression system of claim 1, wherein the DNA sequence encoding the Sc-IndC protein is a sequence at least 85% identical to the sequence set forth in SEQ ID NO:3.

13. A method for synthesizing a blue pigment indigoidine, the method comprising:
   co-expressing a Sc-IndB protein and a Sc-IndC protein in a heterologous host cell,
   wherein the Sc-IndB protein has at least 85% identity to the amino acid sequence set forth in SEQ ID NO:2, and the Sc-IndC protein has at least 85% identity to the amino acid sequence set forth in SEQ ID NO:4.

14. The method of claim 13, wherein the heterologous host is a bacterium.

15. The method of claim 13, wherein the heterologous host further comprises a nucleotide sequence that encodes a *Bacillus subtilis*-derived sfp gene.

16. The method of claim 13, wherein the heterologous host expresses a phosphopantetheinyl transferase (PPTase).

17. The expression system of claim 1, wherein:
   the Sc-IndB protein is encoded by the amino acid sequence set forth in SEQ ID NO:2, and
   the Sc-IndC protein is encoded by the amino acid sequence set forth in SEQ ID NO:4.

18. The expression system of claim 1, wherein:
   the DNA sequence encoding the Sc-IndB protein is the sequence set forth in SEQ ID NO:1, and
   the DNA sequence encoding the Sc-IndC protein is the sequence set forth in SEQ ID NO:3.

* * * * *